United States Patent
Wang et al.

(10) Patent No.: US 10,301,613 B2
(45) Date of Patent: May 28, 2019

(54) TARGETED REMODELING OF PROKARYOTIC GENOMES USING CRISPR-NICKASES

(71) Applicant: Arizona Board of Regents on behalf of Arizona State University, Scottsdale, AZ (US)

(72) Inventors: Xiao Wang, Chandler, AZ (US); Kylie Standage-Beier, Phoenix, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 15/260,788

(22) Filed: Sep. 9, 2016

(65) Prior Publication Data

US 2017/0073663 A1    Mar. 16, 2017

Related U.S. Application Data

(60) Provisional application No. 62/219,117, filed on Sep. 15, 2015.

(51) Int. Cl.
  *C12N 15/01*    (2006.01)
  *C12N 9/22*     (2006.01)

(52) U.S. Cl.
  CPC .............. *C12N 15/01* (2013.01); *C12N 9/22* (2013.01)

(58) Field of Classification Search
  None
  See application file for complete search history.

(56) References Cited

U.S. PATENT DOCUMENTS

2012/0220000 A1    8/2012    Gong et al.

OTHER PUBLICATIONS

Wang et al., Hydrodynamics of diamond-shaped gradient nanopillar arrays for effective DNA translocation into nanochannels., ACS Nano, 2015, 9(2):1206-18.
Raeside et al., Large Chromosomal Rearrangements during a Long-Term Evolution Experiment with *Escherichia coli*., mBio, Sep. 2014, 5(5):e01377-14.
Barrick et al., Genome evolution and adaptation in a long-term experiment with *Escherichia coli*., Nature, Oct. 2009, 461:1243-7.
Darling et al., Dynamics of Genome Rearrangement in Bacterial Populations., PLOS Genetics, Jul. 2008, 4(7):e1000128(16 pages).
Cooper et al., Mechanisms causing rapid and parallel losses of ribose catabolism in evolving populations of *Escherichia coli* B., Journal of Bacteriology, May 2001, 183(9):2834-41.
Riehle et al., Genetic architecture of thermal adaptation in *Escherichia coli*., PNAS, Jan. 2001, 98(2):525-30.
Enyeart et al., Generalized bacterial genome editing using mobile group II introns and Cre-lox., Molecular Systems Biology, 2013, 9:685.
Kolisnychenko et al., Engineering a reduced *Escherichia coli* genome., Genome Research, Apr. 2002, Genome Research, 12(4):640-7.
Cong et al., Multiplex Genome Engineering Using CRISPR/Cas Systems., Science, 2013, 339(6121):819-23.
Mali et al., RNA-guided human genome engineering via Cas9., Science, Feb. 2013, 339(6121):823-6.
Jiang et al., RNA-guided editing of bacterial genomes using CRISPR-Cas systems., Nature Biotechnology, 2013, 31(3):233-9.
Makarova et al., Evolution and classification of the CRISPR-Cas systems., Nature Reviews Microbiology, Jun. 2011, 9(6):467-77.
Barrangou et al., CRISPR provides acquired resistance against viruses in prokaryotes., Science, Mar. 2007, 315(5819):1709-12.
Marraffini and Sontheimer, CRISPR interference limits horizontal gene transfer in staphylococci by targeting DNA., Science, Dec. 2008, 322(5909):1843-5.
Sapranauskas et al., The *Streptococcus thermophilus* CRISPR/Cas system provides immunity in *Escherichia coli*., Nucleic Acids Research, 2011, 39(21):9275-82.
Mojica et al., Short motif sequences determine the targets of the prokaryotic CRISPR defence system., Microbiology, Mar. 2009, 155(Pt. 3):773-40.
Marraffini and Sontheimer, Self vs. non-self discrimination during CRISPR RNA-directed immunity., Nature, 2010, 463(7280): 568-571.
Citorik et al., Sequence-specific antimicrobials using efficiently delivered RNA-guided nucleases., Nature Biotechnology, 2014, 32(11):1141-5.
Caliando and Voigt, Targeted DNA degradation using a CRISPR device stably carried in the host genome., Nature Communications, May 2015, 6:6989(10 pages).
Edgar and Qimoron, The *Escherichia coli* CRISPR System Protects from λ Lysogenization, Lysogens, and Prophage Induction., Journal of Bacteriology, Dec. 2010, 192(23):6291-4.
Vercoe et al., Cytotoxic Chromosomal Targeting by CRISPR/Cas Systems Can Reshape Bacterial Genomes and Expel or Remodel Pathogenicity Islands., PLOS Genetics, Apr. 2013, 9(4):e1003454(13 pages).
Oh and Van Pijkeren, CRISPR-Cas9-assisted recombineering in Lactobacillus reuteri., Nucleic Acids Research, Sep. 2014, 42(17):e131(11 pages).
Sharan et al., Recombineering: a homologous recombination-based method of genetic engineering., Nature Protocols, 2009, 4(2)::206-23.
Mosberg et al., Lambda red recombineering in *Escherichia coli* occurs through a fully single-stranded intermediate., Genetics, Nov. 2010, 186(3):791-9.

(Continued)

*Primary Examiner* — Nancy A Treptow
(74) *Attorney, Agent, or Firm* — Rodney J. Fuller; Booth Udall Fuller, PLC

(57) ABSTRACT

The present invention relates to kits and methods of modifying the prokaryotic genome a Clustered Regularly Interspaced Short Palindromic Repeats (CRISPR)-Cas system that utilized one nicking Cas nuclease and crRNAs. The kid and methods delete or replace portions of the prokaryotic genome. In some embodiments, an entire gene or multiple genes may be deleted or replaced.

16 Claims, 20 Drawing Sheets

Specification includes a Sequence Listing.

(56) References Cited

OTHER PUBLICATIONS

Wang et al., Programming cells by multiplex genome engineering and accelerated evolution., Nature, Aug. 2009, 460(7257):894-8.
Issacs et al., Precise manipulation of chromosomes in vivo enables genome-wide codon replacement., Science, Jul. 2011, 333(6040):348-53.
Datsenko and Wanner, One-step inactivation of chromosomal genes in *Escherichia coli* K-12 using PCR products., PNAS USA, Jun. 2000, 97(12):6640-5.
Baba et al., Construction of *Escherichia coli* K-12 in-frame, single-gene knockout mutants: the Keio collection., Molecular Systems Biology, 2006, 2:2006.0008(11 pages).
Jinek et al., A programmable dual-RNA-guided DNA endonuclease in adaptive bacterial immunity., Science, Aug. 2012, 337(6096):816-21.
Ran et al., Double nicking by RNA-guided CRISPR Cas9 for enhanced genome editing specificity., Cell, Sep. 2013, 154(6):1380-9.
Mali et al., CAS9 transcriptional activators for target specificity screening and paired nickases for cooperative genome engineering., Nature Biotechnology, Sep. 2013, 31(9):833-8.
Qi et al., Repurposing CRISPR as an RNA-guided platform for sequence-specific control of gene expression., Cell, Feb. 2013, 152(5):1173-83.
Chen et al., Characterization of 582 natural and synthetic terminators and quantification of their design constraints., Nature Methods, Jul. 2013, 10(7):659-64.
Lovett et al., A sister-strand exchange mechanism for recA-independent deletion of repeated DNA sequences in *Escherichia coli*., Genetics, Nov. 1993, 153(3):631-42.
Shapiro, Letting *Escherichia coli* teach me about genome engineering., Genetics, Dec. 2009, 183(4):1205-14.
Redder and Linder, New Range of Vectors with a Stringent 5-Fluoroorotic Acid-Based Counterselection System for Generating Mutants by Allelic Replacement in *Staphylococcus aureus*., Applied and Environmental Microbiology, Jun. 2012, 78(11):3846-54.
Way et al., Integrating biological redesign: where synthetic biology came from and where it needs to go., Cell, Mar. 2014, 157(1):151-61.
Pal et al., The dawn of evolutionary genome engineering., Nature Reviews Genetics, Jul. 2014, 15:504-12.
Lu et al., Next-generation synthetic gene networks., Nature Biotechnology, Dec. 2009, 27(12):1139-50.
Mishra et al., A load driver device for engineering modularity in biological networks., Nature Biotechnology, Dec. 2014, 32(12):1268-75.
Hacker et al., Pathogenicity islands of virulent bacteria: structure, function and impact on microbial evolution., Molecular Microbiology, Mar. 1997, 23(6):1089-97.
Lu and Collins, Engineered bacteriophage targeting gene networks as adjuvants for antibiotic therapy., PNAS, Mar. 2009, 106(12):4629-34.
Farzadfard and Lu, Genomically Encoded Analog Memory with Precise In vivo DNA Writing in Living Cell Populations., Science, Nov. 2014, 346:6211.
Ellis et al., Diversity-based, model-guided construction of synthetic gene networks with predicted functions., Nature Biotechnology, May 2009, 27(5):465-71.
Litcofsky et al., Iterative plug-and-play methodology for constructing and modifying synthetic gene networks., Nature Methods, Nov. 2012, 9(11):1077-80.
Stricker et al., A fast, robust and tunable synthetic gene oscillator., Nature, Nov. 2008, 456:516-9.
Payne et al., Temporal control of self-organized pattern formation without morphogen gradients in bacteria., Molecular Systems Biology, 2013, 9:697(10 pages).
Wu et al., Engineering of regulated stochastic cell fate determination., PNAS, Jun. 2013, 110(26):10610-5.
St-Pierre et al., One-Step Cloning and Chromosomal Integration of DNA., ACS Synthetic Biology, 2013, 2(9):537-41.
Mahalakshmi et al., yciM is an essential gene required for regulation of lipopolysaccharide synthesis in *Escherichia coli*., Molecular Microbiology, 2014, 91(1):145-57.
Standage-Beier et al., Targeted Large-Scale Deletion of Bacterial Genomes Using CRISPR-Nickases., ACS Synthetic Biology, Nov. 2015, 4(11):1217-25.

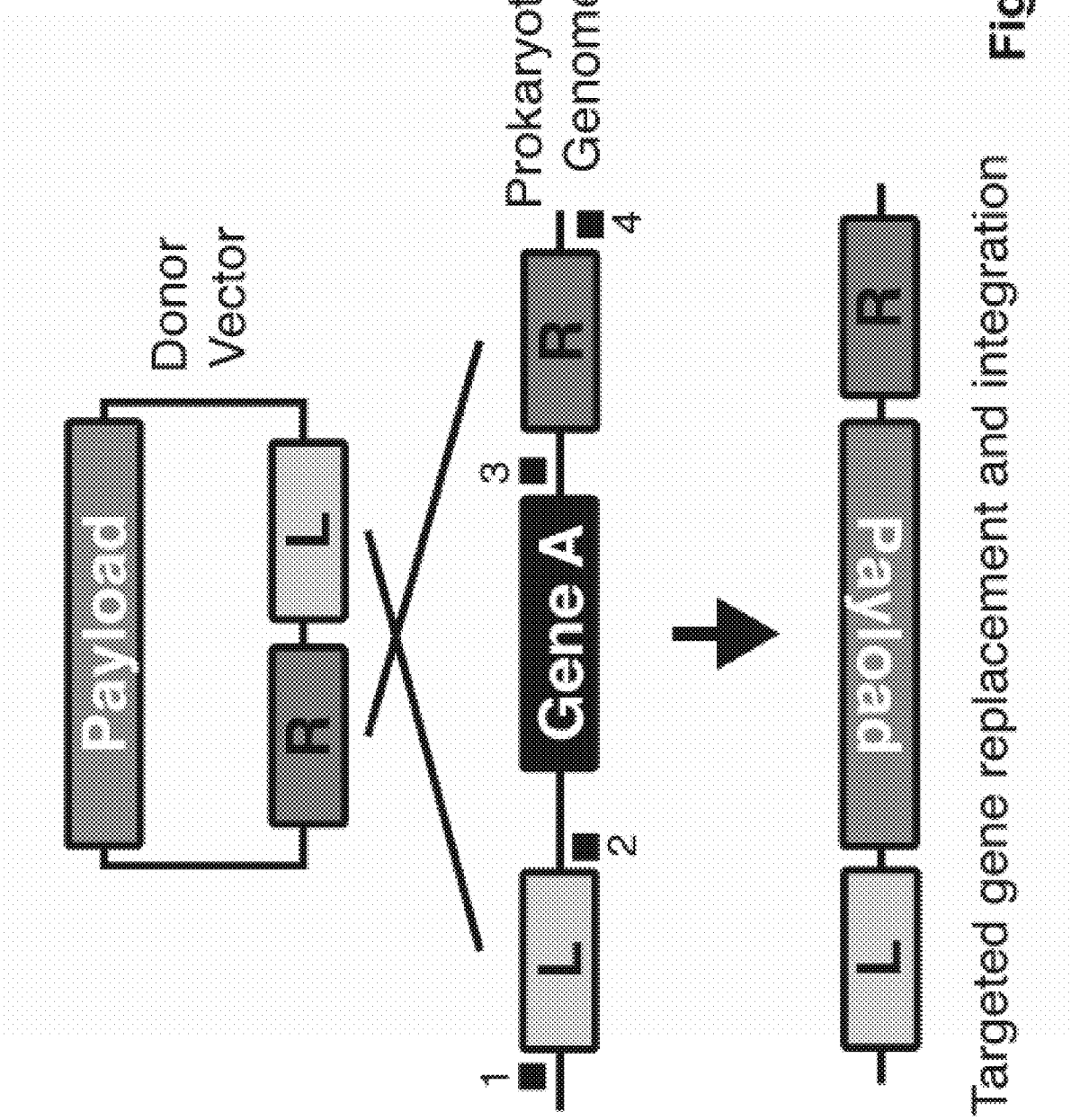

TARGETED REMODELING OF PROKARYOTIC GENOMES USING CRISPR-NICKASES

RELATED APPLICATION DATA

This application claims priority to and the benefit of U.S. Provisional Application No. 62/219,117 filed Sep. 15, 2015, the contents of which are hereby incorporated by reference in their entirety.

GOVERNMENTAL SUPPORT OF APPLICATION

This invention was made with government support under R01 GM106081 awarded by the National Institutes of Health and 1100309 awarded by the National Science Foundation. The government has certain rights in the invention.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 13,915 byte ASCII (text) file named "11157_011SeqList" created on Jul. 29, 2016.

FIELD OF THE INVENTION

The present invention relates to the remodeling of prokaryotic genomes using a Clustered Regularly Interspaced Short Palindromic Repeats (CRISPR)-CRISPR-associated (Cas) system. In particular, this present invention relates to large-scale remodeling of the prokaryotic genome.

BACKGROUND OF THE INVENTION

Large chromosomal rearrangements and deletions have been observed in both natural and laboratory bacterial evolution studies (1-3) and shown to have profound impacts on bacterial physiology, such as improved bioproduct production (4), increased strain fitness (5), or changed tolerance to stress (6). However, such desired genotypes can only be produced in the lab by time-consuming and laborious directed evolution experiments. This is because bacterial genome rearrangement and deletion events only occur when a spontaneous but stochastic DNA break emerges between direct-repeat sequences (3). Currently technologies for remodeling bacterial genome lack efficient methods for targeted large-scale genome remodeling. The genome-remodeling strategies in synthetic biology rely on the use of recombinases or meganucleases (7, 8, 23-27); however this requires insertion of exogenous recombinase or meganuclease sites into the bacterial genome (23-27). These methods are used for systematic generation of single-gene knockouts (27, 28). Thus there is a deficit of technologies that can target remodeling between endogenous DNA sequences. Inducing recombination in a programmable and controllable fashion without exogenous sequences would broaden and simplify implementations of genome engineering for more applications.

SUMMARY OF THE INVENTION

In general, the invention is directed to methods of editing a target sequence of a prokaryotic genome. The methods typically include introducing a first nucleotide sequence encoding a nuclease encoded by a Clustered Regularly Interspaced Short Palindromic Repeats (CRISPR)-associated gene into the prokaryotic cell and a second nucleotide sequence encoding a crRNA into prokaryotic cell. The crRNA typically preferably includes a guide sequence complementary to a region of the prokaryotic target sequence that is less than 100 nucleotides from a repeated or homologous prokaryotic sequence. The prokaryotic target sequence is also directly next to a protospacer adjacent motif (PAM). The nuclease introduced into the prokaryotic cell includes a nicking nuclease.

The methods of the invention further include coexpressing the first and second nucleotide sequences in the prokaryotic cell to generate a transformed prokaryotic cell. The methods also preferably include culturing the transformed prokaryotic cell. Typically, during the culturing step, the target sequence is removed from the genome of the cultured prokaryotic cell.

In certain non-limiting implementations of the method of editing a target sequence in a prokaryotic cell genome, the second nucleotide sequence encodes at least one pair of crRNAs. One member of the at least one pair of crRNAs may include a guide sequence complementary to the 5' end of the target sequence while the other member may advantageously include a guide sequence complementary to the 3' end of the target sequence. In these particular implementations of the invention, culturing the transformed prokaryote deletes the target sequence from the prokaryotic cell genome.

In a particular embodiment, the methods of editing a target sequence in a prokaryotic cell genome preferably includes introducing a third nucleotide sequence encoding a donor sequence, wherein the donor sequence comprises the repeated or homologous sequence of the prokaryotic genome, and a replacement sequence. In this particular embodiment and certain other implementations, the coexpressing step involves coexpressing the first, second, and third nucleotide sequences in the prokaryotic cell to generate a transformed prokaryotic cell. Culturing the transformed prokaryotic cell in these particular embodiments replaces the target sequence with the replacement sequence in the genome of the cultured prokaryotic cell.

The invention is also directed to methods of editing at least two target sequences of the genome of a prokaryotic cell. These methods comprise introducing a first nucleotide sequence encoding a nuclease encoded by a CRISPR-associated gene into the prokaryotic cell, wherein the nuclease is a nicking nuclease; a second nucleotide sequence encoding a first pair of crRNAs into prokaryotic cell, wherein the first pair of crRNAs comprise two guide sequences complementary to regions at the 5' end and 3' end of a first target sequence of the prokaryotic genome that is less than 100 nucleotides from two separate repeated or homologous sequence of the prokaryotic genome and directly next to a PAM; and a third nucleotide sequence encoding a second pair of crRNAs into prokaryotic cell, wherein the second pair of crRNAs comprise two guide sequences complementary to regions at the 5' end and 3' end of a second target sequence of the prokaryotic genome that is less than 100 nucleotides from two separate repeated or homologous sequence of the prokaryotic genome and directly next to a PAM. The methods further comprise coexpressing the first, second, and third nucleotide sequences in the prokaryotic cell to generate transformed prokaryotic cell; and culturing the transformed prokaryotic cell. During the culturing step, the first and second target sequences are removed from the genome of the prokaryotic cell. In some implementations, culturing the transformed prokaryotic cell deletes the first and second target sequences from the genome of the prokaryotic cell.

In other implementations, culturing transformed prokaryotic cell replaces the first and/or second target sequences with a replacement sequence. In these implementations, the method of editing at least two target sequences of the genome of a prokaryotic cell further comprises introducing a fourth nucleotide sequence encoding a donor sequence and the replacement sequence. The donor sequence comprises the repeated or homologous sequence of the prokaryotic genome. Accordingly, the coexpressing step of these implementations involves coexpressing the first, second, third, and fourth nucleotide sequences in the prokaryotic cell to generate a transformed prokaryotic cell.

The target sequence is preferably less than 50 nucleotides from a repeated or homologous sequence of the prokaryotic genome in the methods described herein. For example, the target sequence may be between 20 to 40 nucleotides, 25 to 35 nucleotides, 30 to 45 nucleotides, or 20 nucleotides from a repeated or homologous sequence of the prokaryotic genome.

In certain preferred embodiments, the crRNA is preferably an sgRNA comprising an 18 to 22-nucleotide long guide sequence. Additionally, the nicking nuclease is preferably Cas9 comprising either a mutation in its RuvC1 nuclease domain or a mutation in its HNH nuclease domain. Also, preferably the mutation is either a D10A or a H840A mutation.

In the methods described herein, a 36 Kb to 97 Kb portion of the genome of the prokaryotic cell may be deleted, for example a 36 Kb portion or a 97 Kb portion. In embodiments where at least two target sequences of the genome of a prokaryotic cell are edited, a 133 Kb portion of the genome of the prokaryotic cell may be deleted.

Only one kind of nicking nuclease is typically introduced in the methods of the invention. Thus, preferably the CRISPR-Cas system selected and used in the methods of the invention, only make single-stranded breaks in the prokaryotic genome. The methods of the invention do not utilize a combination of nicking nucleases like the CRISPR-Cas systems used to edit eukaryotic genomes to generate double-stranded DNA breaks.

BRIEF DESCRIPTION OF THE DRAWINGS

FIG. 1A depicts a schematic representation of sgRNA guided Cas9s targeting a chromosomally integrated GFP reporter. The sgRNA guide sequence is visualized adjacent to its target sequence. The protospacer adjacent motif (PAM) sequence is underlined. Arrows denote where DNA cleavage occurs by two Cas9 mutants, respectively. Cas9D10A cleaves the target DNA strand complimentary to the sgRNA and Cas9H840A cleaves the non-complimentary strand. FIG. 1B depicts the transformation efficiencies of sg(C1) (gray) or untargeted sg(-) (white) in K12 E. coli containing Cas9WT, CasD10A, Cas9H840A, or dCas9. Error bars represent ±standard deviation (n=3).

FIG. 2A depicts diagram of chromosomally integrated dual-fluorescent reporter with internal homologous DNA sequences (R), shown as dark and light gray boxes. sgRNA-guided Cas9 nicking enzyme generates an SSB, illustrated by the scissor. CRISPR induced deletions of GFP results in the joining of two repeats, shown as a gray box with both dark and light shades. Primers (Pr1 and Pr4) flank the dual fluorescence reporter. FIG. 2B depicts flow cytometry screening of pooled sgRNA transformations for homologous recombination. Histograms show population fluorescence distributions for controls sg(-) (dark gray), cells containing RFP with no GFP (light gray), and sg(T1) coexpressed with Cas9D10A (black line). Vertical dashed line represents threshold for GFP expression. 86% of sg(T1) cells fall to the left of the line, indicating the loss of GFP expression. The graph of FIG. 2C shows the percent of flow cytometry estimated GFP deletion for various sgRNA targets using Cas9D10A (light gray) and Cas9H840A (dark gray). Nicking sites within GFP are represented by grayscale triangles, and sgRNA binding sites within GFP are represented by black squares. Cut positions are defined as base pairs (bp) from the left repeat. FIG. 2D depicts fluorescence microscopy interrogation of dual-fluorescent reporter expression for sg(-) and sg(T1) transformants in E. coli expressing Cas9D10A. GFP expression is undetectable in sg(T1) while RFP expression is similar in both sg(-) and sg(T1). Phase contrast images show cells are healthy for both conditions. FIG. 2E depicts gel-electrophoresis of amplicons using primers Pr1 and Pr4 from transformants for sg(T1) and sg(-). The primers generate a 4.6 kilobases (Kb) amplicon for the initial RFP:GFP site and following HR the primers generate a 3.6 Kb amplicon. Six out of six sg(T1) transformants amplify at sizes of approximately 3.6 Kb, while a sg(-) control template results in banding at 4.6 Kb.

FIG. 3A depicts a schematic representation of a 36.8 Kb genomic region with two IS5 direct-repeats (gray, R) on the K12 MG1655 chromosome at the top and the results of CRISPR induced deletion of genomic region between two repeats (shown gray box with mixed shades) at the bottom. Colored boxes serve as visual aids to mark relative positions and sizes of various genomic regions. A series of 10 sgRNAs were designed to target various locations (black squares, sg(A-J)). Primers flanking each repeat ($P^h1$-$P^h4$) are used for PCR based genotyping of chromosomal deletions. The His biosynthetic operon (His-Operon) located between the IS5 elements serves as a screenable marker for cells harboring deletions. FIG. 3B depicts a representative schematic representation of multi-targeting nicking systems around the left IS5, with 3' Overhang (OH) and 5' OH cut orientations highlighted. "Bp apart" is the base pair distance between cut sites. Blue triangles indicate cut sites for respective guides. FIG. 3C depicts the results of PCR screening and gel electrophoresis of pooled transformations to detect formation of recombined site (mixed gray icons) using primers Ph1 and Ph4. FIG. 3D depicts the results of histidine auxotrophy screening of individual isolated transformants expressing Cas9D10A with sg(B:I) and sg(A:B). Differential growth on M9 minimal medium containing synthetic complete amino acids (M9SC) or M9 without histidine (M9-H) suggests deletions of the targeted region when no colonies are formed in M9-H. Colony positions on M9SC correspond to those on M9-H. Success rates are denoted as the number of colonies unable to grow in M9-H over the total number of colonies. FIG. 3E depicts PCR genotyping of 6 sg(B:I) histidine auxtrophs and a control sg(-) transformant using 3 different primer combinations confirming formation of the recombined site (bottom row).

FIG. 4A depicts a schematic view of two separate genomic regions surrounded by direct repeat sequences. Definitions of illustrations are the same as in FIGS. 3A-E. The middle disjoint box represents 670 Kb distance between these two regions. The left region is 97 kilobases and contains the tryptophan biosynthesis operon (TRP) and the pyrF gene (labeled bright blue boxes). Recombination between these repeats results in deletion of 97 Kb (Δ97 Kb) and tryptophan auxotrophy. The remodeled site (mixed gray R) brings primers Pt1 and Pt4 into close proximity. sgRNAs K and L target the sequences directly adjacent to the left repeat to this region. In parallel, guides B and I target a separate region containing His, (see FIGS. 3A-E also). Deletion of this region results in a loss of 36 Kb (Δ36 Kb) and histidine auxotrophy. The remodeled sequence results in close proximity of Ph1 and Ph4. FIG. 4B depicts PCR monitoring of HR in Cas9D10A expressing cells. Primers Pt1 and Pt4 detect deletion of 97 Kb (resulting in a 1.5 Kb amplicon). Ph1 and Ph4 detect recombination across 36 Kb (resulting in a 1.8 Kb amplicon). Different sgRNA targets are indicated beneath the gel photo. sg(−) is a guide sequence not matching the bacterial genome. Amplification indicates occurrence of recombination. FIG. 4C depicts the resulting phenotypes of isolated *E. coli* containing different remodeling combinations. Cells isolated containing different deletions replica plated on M9 synthetic complete medium (M9SC), M9 lacking histidine (M9-H), and M9 without tryptophan (M9-T). Vertical columns correspond to different deletions. sg(−) with no genomic deletion (Δ0) serves as the control. sg(B:I:K:L) expressing cells can harbor 36 (Δ36), 97 (Δ97) or combined 133 kilobase (Δ133) deletions. Δ36, Δ97 and Δ133 are auxotrophic histidine, tryptophan and both, respectively.

FIG. 5 depicts a schematic of gene replacement and integration using CRISPR-Cas systems. A Plasmid "Donor Vector" contains two sequences "R and L" homologous to the prokaryotic genome flanking a gene "Gene A" and a payload sequence. The payload sequence may comprise genes encoding antibiotic resistance markers, synthetic gene circuits, or biosynthetic pathways. The nicking Cas nuclease targets sites 1 through 4 (black squares) to induce recombination between the Donor Vector and the prokaryotic genome. This results in replacement of "Gene A" with a payload sequence.

FIG. 6A shows maps of nicking CRISPR-Cas dual-plasmid system. pCas9D10A enables target DNA cleavage, while pSG4K5 enables programming of targets. Plasmid pCas9D10A (derived from Addgene #44250) contains an ampicillin resistance marker (AmpR), the tetracycline repressor (TetR), a ColE1 origin of replication, and *Streptococcus pyogenes* Cas9D10A. pSG4K5 is derived from plasmid pSB4K5 (Registry of Standard Biological Parts). The plasmid contains a pSC101 origin of replication, which is compatible with ColE1 plasmids. Also, pSG4K5 contains a kanamycin resistance marker (KanR) and an sgRNA expression cassette. FIG. 6B shows the cloning site for programming of sgRNAs with useful restriction sites for multiplex targeting. DNA duplexes in the format shown (sgRNA guide) allow for ligation into SapI cleaved plasmids. Inverted SapI recognition sites are underlined and 3 nucleotide 5' overhang sites are underlined. The transcriptional start from the promoter is the highlighted light gray "A" (+1) nucleotide. To generate multiplex targeting vectors, digestion of PCR amplified sgRNA cassettes with EcorI and SpeI enables ligation into BsaI cleaved pSG4K5. This allows for modular and repetitive assembly of multiple sgRNAs.

FIG. 7A is a schematic representation of sgRNAs (T1-5) targeting a genome integrated GFP template sequence. FIG. 7B depicts the transformation efficiencies of K12 strains containing Cas9WT, D10A, H840A or dCas9 with different guide sequences. sg(−) is a control guide not matching the genome. It can be seen that DSBs lead to cell death for all five cleavage positions, while SSBs have no effects on cell viability for all five positions.

FIG. 10A depicts sg(T1) coexpression with Cas9D10A (light gray) or Cas9H840A (dark gray). The black square indicates the sgRNA targeting location with light and dark gray triangles representing cut sites of respective Cas9 mutants. FIG. 10B shows flow cytometry of corresponding sg(T1) Cas9 mutants. The dashed line corresponds to gating between GFP positive and negative cells.

FIG. 12A is a schematic representation of a 97 Kb region of the K12 genome containing IS5 sequences (gray, R). The tryptophan biosynthesis operon (TRP) and pyrF genes function as screenable markers. Deletions of 97 Kb (Δ97) result in the formation of the recombined site (mixed gray R), along with close proximity of primers Pt1 and Pt4. Guides K and L target adjacent to the left IS5 (See FIGS. 4A and 4B also). FIG. 12B depicts the transformation efficiency of single and multitargeted nicking systems into cells expressing Cas9D10A compared to non-targeted, sg(−), control. Dashed line indicates minimum detectable efficiency. Four-targeting transformation does not reduce transformation efficiency. FIG. 12C shows the PCR analysis of single and cooperative nicking induced recombination. Remodeling of repeat sequences results in proximity of Pt1 and Pt4 leading to a 1.5 Kb PCR amplicon. The first lane is DNA ladder, with following lanes corresponding to cells expressing different guide combinations. FIG. 12D depicts the screening and isolation of 97 Kb genomic deletions. The fraction of 5-FOA resistant (5-FOAR) colonies to total number of cells was determined by serial dilution plating on media with and without 5-FOA. Subsequent tryptophan auxotrophy screens using 5-FOAR colonies. Cropped plate photos of tryptophan auxotrophy screens with M9 synthetic complete (M9SC) and M9 lacking tryptophan (M9-T) (n=100 colonies).

DETAILED DESCRIPTION OF THE INVENTION

Figure 1A:
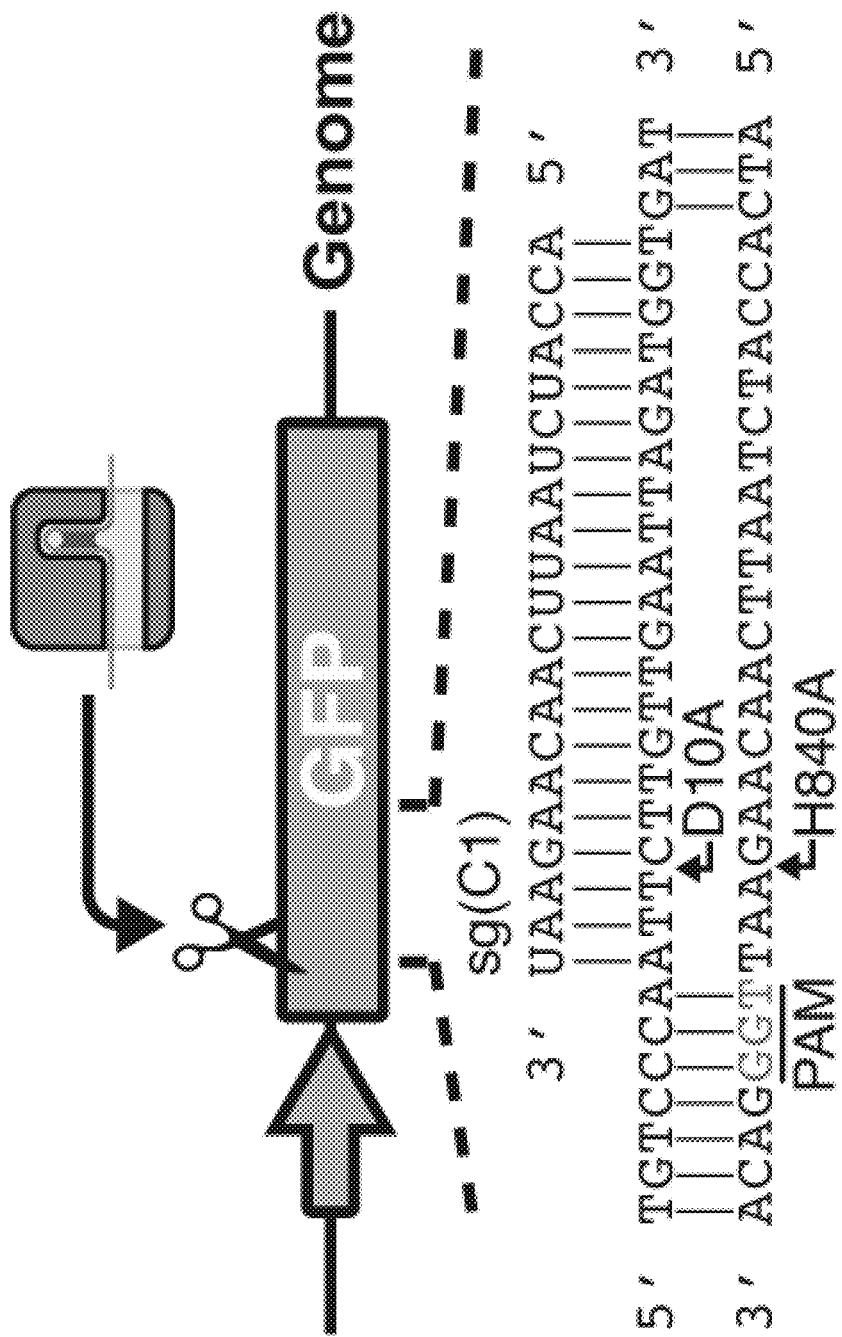
FIGS. 1A and 1B show that CRISPR-directed SSBs are not lethal to K12 E. coli.

Detailed aspects and applications of the invention are described below in the drawings and detailed description of the invention. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the invention. It will be understood, however, by those skilled in the relevant arts, that the present invention may be practiced without these specific details. It should be noted that there are many different and alternative configurations, devices and technologies to which the disclosed inventions may be applied. The full scope of the inventions is not limited to the examples that are described below.

The singular forms "a," "an," and "the" include plural referents unless the context clearly dictates otherwise. Thus, for example, reference to "a step" includes reference to one or more of such steps.

As used herein, the terms "nickase" or "nicking nuclease" refers to an endonuclease that is only capable of making single-stranded breaks (SSBs) in DNA rather than double-stranded breaks (DSBs). Thus a "nicking Cas nuclease" refers to a nuclease encoded by CRISPR-associated genes that can only make SSBs. Such nuclease may naturally be limited to making SSBs or they may be mutated nucleases rendered to only make SSBs.

The term "prokaryote" refers to single-celled organisms that lack a membrane-bound nucleus or any membrane-bound organelle. Prokaryote includes organisms in the archaea and bacteria domains. In preferred embodiments, prokaryote refers to bacteria.

The term "repeated sequence" as used herein refers to any patterns of nucleic acids that occur in multiple copies throughout the genome of the prokaryote. These include simple sequence repeats.

As used herein, "transform" and "transformation" refer to the transfer of a nucleic acid molecule into a host organism. In preferred embodiments, the nucleic acid molecule is stably maintained or integrated into the genome of the host organism. Host organisms containing the transformed nucleic acid fragments are referred to as "transgenic" or "recombinant" or "transformed" or "transformant" organisms.

The terms "plasmid" and "vector" refer to an extra chromosomal element often carrying genes that are not part of the central metabolism of the cell, thus not part of the microbial genome. Usually, plasmids and vectors are in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction that is capable of introducing an expression cassette(s) into a cell.

The replacement of one amino acid with another amino acid at a particular amino acid residue number in a protein sequence is depicted in the format: (single letter abbreviation for the original amino acid)(residue number)(single letter abbreviation for the replacement amino acid). For example, replacement of aspartic acid with alanine at amino acid residue 10 would be depicted as D10A.

The present invention arises from the discovery that single-stranded DNA cleavage (nicking of the DNA) does not inflict lethal damage in wild-type bacteria and that the Clustered Regularly Interspaced Short Palindromic Repeat (CRISPR)-CRISPR-associated (Cas) system may be modified for use in prokaryotes.

The CRISPR-Cas system functions as a prokaryotic and archaeal immune system that protects cells from foreign nucleic acids (12-14). CRISPR RNAs (crRNAs) direct degradation of target DNAs through simple Watson-Crick base pairing to recruit a nuclease, such as nucleases or helicases encoded by CAS genes to introduce double stranded DNA breaks (DSBs) to foreign nucleic acids (13-15), which results in gene silencing similar to the RNA interference mechanisms seen in eukaryotic organisms. These systems have minimal sequence targeting constraints, requiring only a small proto-spacer adjacent motif (PAM) sequence (16, 17), so it is possible to program CRISPR-Cas system to target almost any sequence.

The CRISPR-Cas system has been adapted for gene editing in eukaryotes by taking advantage of the eukaryotic organism's DNA repair mechanisms. When the systems are used for gene editing in eukaryotes, a crRNA is created to direct the CAS nuclease, for examples Cas9, to the targeted gene. Upon binding to crRNA, the nuclease introduces a DSB to the target gene. Even though crRNA is able to guide the nuclease to the desired site for the DSB, there is a high incidence of off-target cleavage. For increased accuracy, two crRNA are used to guide nucleases mutated so that they each nick one of the strands of the DNA (hereinafter "nicking nucleases"). The use of two crRNA reduces the incidence of off-targeting cleavage. Thus even though nicking CAS nucleases are used in eukaryotic genome editing, the ultimate goal is still making DSBs in the eukaryotic genome. When the eukaryotic cell's DNA repair mechanism fixes the DSB by rejoining the two ends, a one to 100 base pairs are deleted. This results in the target gene being incapable of producing a functional protein, or the mutated target gene produces protein products that are constitutively active. Accordingly, gene editing in eukaryotic cells by the CRISPR-Cas system is limited to remove at most 100 base pairs to affect the function of the target gene. Because the CRISPR-Cas system depends on the eukaryotic cell's DNA repair mechanism, the system cannot remove entire gene from the eukaryotic cell's genome.

When the CRISPR-Cas system is turned onto gene editing of the prokaryotic genome, the results are deadly (11, 18-21). Most prokaryotes lack DNA repair mechanism to address DSBs, so targeting the CAS nuclease to a gene of the prokaryotic genome is lethal to the organism. Thus currently, the use of the CRISPR-Cas system in prokaryotes has been a method of screening for desired mutations (11, 12). However, the discovery that nicking of the prokaryotic genome is not lethal to the prokaryotic cell allows the use of the CRISPR-Cas system to delete or replace genes of the prokaryotic genome.

The invention is directed to methods and kits for modifying the genomes of prokaryotes using CAS nucleases modified to make only SSBs in the prokaryotic genome. These SSBs trigger the homologous recombination in the prokaryotic genome to result in gene deletion and/or replacement. Thus the genome of any bacteria capable of homology recombination may be edited by the methods of the invention. Accordingly, the methods comprise introducing into a prokaryotic cell a nucleotide sequence encoding a nicking Cas nuclease into the prokaryotic cell and a nucleotide sequence encoding a crRNA into prokaryotic cell. Methods of introducing nucleotides into the genome of a prokaryotic cell are well known the prior art. For example, the prokaryotic cell may be transformed with electroporation, heat-shock, or by phages. In some embodiments, the nucleotides encoding the nicking CAS nuclease and the crRNA are introduced into the prokaryotic genome by separate vectors. However, these nucleotides may also be introduced into the prokaryotic cell by a single vector.

The methods further comprise coexpressing the nicking nuclease and the crRNA in the prokaryotic cell to generate a transformed prokaryotic cell. Culturing of the transformed prokaryotic cell results in the generation of the SSBs in the prokaryotic genome and the homologous recombination that removes a portion of the prokaryotic genome. The methods may be multiplexed by introducing multiple crRNAs to direct recombination of multiple portions of prokaryotic genome. Where multiple crRNAs are expressed into the prokaryotic cell, the nucleotides encoding the crRNAs maybe introduced into the prokaryotic cell by a single expression vector or by multiple expression vectors. Accordingly, the limit on the number of crRNAs that may be introduced into the prokaryotic cell depends on the prokaryotic cell itself and the expression vector.

The kits of for prokaryotic gene editing comprise a nucleotide sequence encoding the nicking Cas nuclease and at least one other nucleotide sequence encoding a crRNA. In embodiments where gene replacement is desired rather than gene deletion, the kits may comprise a third nucleotide sequence encoding a donor sequence, wherein the donor sequence comprises the repeated sequence of the prokaryotic genome, and a replacement sequence. In some implementations for gene replacement, rather than a third nucleotide sequence encoding a donor sequence, the kit comprises a vector comprising a first homologous sequence, a second homologous sequence, and a replacement sequence. The first and second homologous sequences in the vector are homologous to a portion of the genome of the prokaryotic.

The Nicking Cas Nuclease

Non-limiting examples of a Cas nuclease include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4.

So that any gene edit does not result in the death of the prokaryotic cell, the CRISPR-Cas system introduced into the prokaryotic cell only makes SSBs either in the DNA strand complementary to the crRNA or in the DNA strand that is non-complementary to the crRNA. Accordingly, unlike the use of the CRISPR-Cas system for gene editing of eukaryotes, the methods of the invention require that the Cas nuclease introduced into the prokaryotic cell does not produce any DSBs. Thus the Cas nuclease should be modified, if necessary, so that it is only capable of making SSBs. For example, if the Cas nuclease is Cas9, the methods of the invention require the introduced Cas9 contains either an inactive RuvCl domain or an inactive HNH domain. If the goal is cleaving the DNA strand of the prokaryotic genome that is complementary to the crRNA, only a Cas9 with a mutation in the RuvCl domain, for example by a D10A mutation, would be introduced and expressed in the prokaryotic cell. On other hand, if the goal is cleaving the DNA strand of the prokaryotic genome that is non-complementary to the crRNA, only a Cas9 with a mutation in the HNH domain, for example by a H840A, N854A, or N863A mutation, would be introduced into the prokaryotic cell.

The crRNA

Because gene editing in prokaryotes according to the methods of the invention involves homologous recombination, the guide sequences of the crRNA be complementary to a region of the portion of the prokaryotic genome targeted for gene editing that is within 100 nucleotides from a repeated or homologous sequence of the prokaryotic genome. Furthermore, as with all crRNA, the complementary sequences on the prokaryotic genome to the guide sequence must be directly next to a PAM sequence (see FIG. 1A). Preferably, the guide sequence of the crRNA is complementary to a region of the portion of the prokaryotic genome targeted for gene editing that is within 50 nucleotides from a repeated or homologous sequence of the prokaryotic genome, for example between 20-40 nucleotides, or about 20 nucleotides from a repeated or homologous sequence of the prokaryotic genome. The guide sequence should be between 18 to 22 nucleotides long, preferably 20 nucleotides. In preferred embodiments, the crRNA is a short guide RNA (sgRNA).

While a single SSB in the prokaryotic genome may induce homologous recombination to result in the removal of portions of the prokaryotic genome, a preferred implementation of the methods utilized a pair of crRNA for more targeted homologous recombination. The crRNAs in these implementations flank the portion of the prokaryotic genome targeted for removal or replacement by homologous recombination (see FIG. 3A). In particular, the guide sequences target the 3' and 5' end of a repeated or homologous sequence on the prokaryotic genome. A pair of crRNA may mark a portion of up to about 100 kilobases (Kb) for removal or replacement, for example, a 97 Kb portion of the prokaryotic genome.

Multiple pairs of crRNA may be used for multiplexed removal and/or replacement of portions of the prokaryotic genome. Thus multiple portions of the prokaryotic genome marked by each pair of the crRNA are removed by the CRISPER-Cas system of the invention. As shown in Example 3, a 133 Kb portion of the prokaryotic genome may be deleted by two pairs of crRNA. One of the pairs of crRNA directed the removal of a 36 Kb section of the prokaryotic genome while the second pair of the crRNA directed the removal of a 97 Kb section of the prokaryotic genome.

The methods of the invention provide a new tool for design and engineering of bacterial genomes (37, 38). The methods of the invention are also desirable to synthetic biology applications (39, 26, 40) by enabling devices capable of targeted genome remodeling in microbial consortia. For example, because pathogenicity islands are often surrounded by direct repeats (41), the methods of the invention may be used to remove pathogenicity islands. These methods could be employed synergistically with systems that antagonize pathogen gene networks (18, 42) to sculpt microbiota both at the population and genome levels. Furthermore, systems employing retron-mediated reverse transcription have enabled genome directed rewriting and memory storage (43). Coupling our system to the output synthetic gene networks (44-47) could enable dynamic remodeling and rewriting of the genome in response to cell fate decisions (48).

The present invention is further illustrated by the following examples that should not be construed as limiting. The contents of all references, patents, and published patent applications cited throughout this application, as well as the s, are incorporated herein by reference in their entirety for all purposes.

EXAMPLES

Example 1. Generation the CRISPR-Cas9 System of the Present Invention

1. Strain and Media

Molecular cloning was conducted using *E. coli* NEB-10-Beta (New England Biolabs, NEB). Maintenance and cloning of vectors containing an R6Kγ origin of replication was conducted in DH5a (Pir⁺). Fluorescent reporter experiments were conducted in K12 MG1655 (ΔLacIΔAraC) HK022 (J04450 and/or 113522) (Registry of Standard Biological Parts). Initial 36 kilobase (kb) deletion experiments were conducted in K12 MG1655 (ΔLacIΔAraC). Experiments involving the 97 kb deletion were conducted in K12 MG1655 (American Type Culture Collection, ATCC, #700926) HK022 (topA, cysB, ribA, fabI), 186 (lapAB). Integrations into HK022 attB and 186 attB sites are described in strain construction section. LB Miller Medium (Sigma Aldrich, Sigma) was supplemented with appropriate antibiotics for plasmid maintenance: ampicillin (100 μg/ml) and/or kanamycin (30 μg/ml). Experiments involving fluorescent microscopy visualization of genome-integrated reporters used M9 Minimal Medium containing 0.2% glycerol. Screening for histidine and tryptophan auxotrophs was done on M9 Minimal Medium 0.4% glucose, 1.5% agar, 2 mg/ml Uracil with synthetic complete (SC) (i.e. Leucine deficient supplement (Clonetech, #630414)+200 mg/L Leucine (Sigma, #L8000), without histidine (-H) or without tryptophan (-T) amino acid supplement (Clonetech, #630415, #630414 respectively). 5-Huoroorotic Acid (5-FOA, Gold Biotechnology, #F-230-5) media was made by supplementing 5-FOA to a final concentration of 600 mg/L and boiling to dissolve in LB agar miller medium. All cell culture was conducted at 37° C. in either a stationary incubator for Petri dishes, or 250 RPM shaker for liquid media unless noted otherwise.

2. Strain Construction

Genome integration of reporters and other genes were conducted using methods described previously (49). Plasmids pOSIP-KH and pOSIP-KO were used to integrate into HK022 and 186 attB sites respectively. Fluorescent reporters (BioBrick #) parts RFP (J04450) and GFP (113522) were cloned into the EcorI and PstI sites of pOSIP-KH. The strain used for 97 Kb remodeling experiments was derived from ATCC, #700926. Integration vectors containing essential genes (28, 50) were created by stepwise cloning of topA: cysB, ribA, and fabI into pOSIP-KH using primers 18 through 23 with corresponding restriction sites indicated in Table 1 and lapAB in pOSIP KO. The lapAB cassette was ligated and integrated in one step. Purified PCR products of primers 24 and 25 were digest with BamHI and SpeI and ligated into pOSIP-KO. Vectors were integrated by transforming ≤10 ng of plasmid into destination strains. Integrations were confirmed at HK022 att with primers 7 and 8, and 186 att with 26 and 27. R6Kγ vectors were propagated as plasmids at 30° C. and integrated at 37° C.

TABLE 1

PCR Primers for plasmid construction and genotyping.

| # | Sequence (5'-3') | Notes (Restriction Sites) |
|---|---|---|
| 1 | TGCCACCTGACGTCTAAGAA (SEQ ID NO: 1) | sgRNA amplification/sequencing forward |
| 2 | AATACCGCCTTTGAGTGAGC (SEQ ID NO: 2) | sgRNA amplification/sequencing reverse |
| 3 | ATGCTCTTCAGCTATCGGCACAAATAGCGTC (SEQ ID NO: 3) | D10A mutation to s.p.Cas9 forward (SapI) |
| 4 | GAGCTCTTCGAGCTAAGCCTATTGAGTATTTCTTATCC (SEQ ID NO: 4) | D10A mutation to s.p.Cas9 reverse (SapI) |
| 5 | GAGCTCTTCGGCCATTGTTCCACAAAGTTTCCTT (SEQ ID NO: 5) | H840A mutation to s.p.Cas9 forward (SapI) |
| 6 | ATGCTCTTCAGGCATCGACATCATAATCACTTAAACG (SEQ ID NO: 6) | H840A mutation to s.p.Cas9 reverse (SapI) |
| 7 | CGCCATATTCATGGTAGGAATCAATGCCTGAGTG (SEQ ID NO: 7) | $P^r$ reporter forward, HK022 att |
| 8 | GGCATCAACAGCACATTCAGTGGTTTACCGTGCG (SEQ ID NO: 8) | $P^r$ reporter reverse, HK022 att |
| 9 | GCTACGTGTTATGAACTTCGAAGA (SEQ ID NO: 9) | RFP towards GFP sequencing |
| 10 | ACATTTACGCGATTAATACTGCGCGTAATATAATT (SEQ ID NO: 10) | $P^h1$ Left IS5 around His forward |
| 11 | ACATCTGGTGGCGCTAATAAATCTGGCAAGTCACA (SEQ ID NO: 11) | $P^h2$ Left IS5 around His reverse |
| 12 | CCAGCCAGGCTAAGCCTCAAGCACAGGTCAATATC (SEQ ID NO: 12) | $P^h3$ right IS5 around His forward |

TABLE 1-continued

PCR Primers for plasmid construction and genotyping.

| # | Sequence (5'-3') | Notes (Restriction Sites) |
|---|---|---|
| 13 | CGGCTTTGGTCATAATAATAATATTGCGGTGGCGT (SEQ ID NO: 13) | P$^h$4 right IS5 around His reverse |
| 14 | GGATTTCCTTAACTGCTTCTCCTCACC (SEQ ID NO: 14) | P$^l$1 Left IS5 around Trp forward |
| 15 | ATTACCAATAAAGAATCGTCTGGCGGT (SEQ ID NO: 15) | P$^l$2 Left IS5 around Trp reverse |
| 16 | TTATCAGGCTCCTCCAGATAATTGTCG (SEQ ID NO: 16) | P$^l$3 right IS5 around Trp forward |
| 17 | GTCTGCACAAGGATTACATCATGATTATG (SEQ ID NO: 17) | P$^l$4 right IS5 around Trp reverse |
| 18 | GCAGGGGACCCGGTCGATGGGTTGTGTC (SEQ ID NO: 18) | topA:cysB forward (KpnI) |
| 19 | CGTCATGTCACTAGTCGAGGCGGGTAATTAGACA (SEQ ID NO: 19) | topA:cysB reverse (SpeI) |
| 20 | GCAGGATTCACTAGTCCTACTACCAGAACGACGGC (SEQ ID NO: 20) | ribA forward (SpeI) |
| 21 | CGTGTTCGCCTCGAGACTGCGGTACGTCTGGCAAT (SEQ ID NO: 21) | ribA reverse (XhoI) |
| 22 | GCAAGTTTCCTCGAGGGCGGGAAGGGGAGAAA (SEQ ID NO: 22) | fabI forward (XhoI) |
| 23 | CGTGGTATTGGCGCCTCTGGGGAGAGGGTTAGGG (SEQ ID NO: 23) | fabI reverse (KasI) |
| 24 | CGTGGTATTGGATCCTTTGTGGGCCATTAACACCACCT (SEQ ID NO: 24) | lapAB forward (BamHI) |
| 25 | CCTATGATCACTAGTTGGGTCGATCTTGTCGACAAAG (SEQ ID NO: 25) | lapAB reverse (SpeI) |
| 26 | CTCATTCGAAACCACCCACCG (SEQ ID NO: 26) | 186 att forward |
| 28 | GATCATCATGTTTATTGCGTGG (SEQ ID NO: 27) | 186 att reverse |
| 38 | CATGGTCTCAAATTAAGCAGCTCTAATGCGCT (SEQ ID NO: 28) | Deltete TetR from pCas9 forward |
| 29 | GACATGTCTAGACAACTTAAATGTGAAAGTGGGTCT (SEQ ID NO: 29) | Deltete TetR from pCas9 reverse (XbaI) |

Figure 6A:
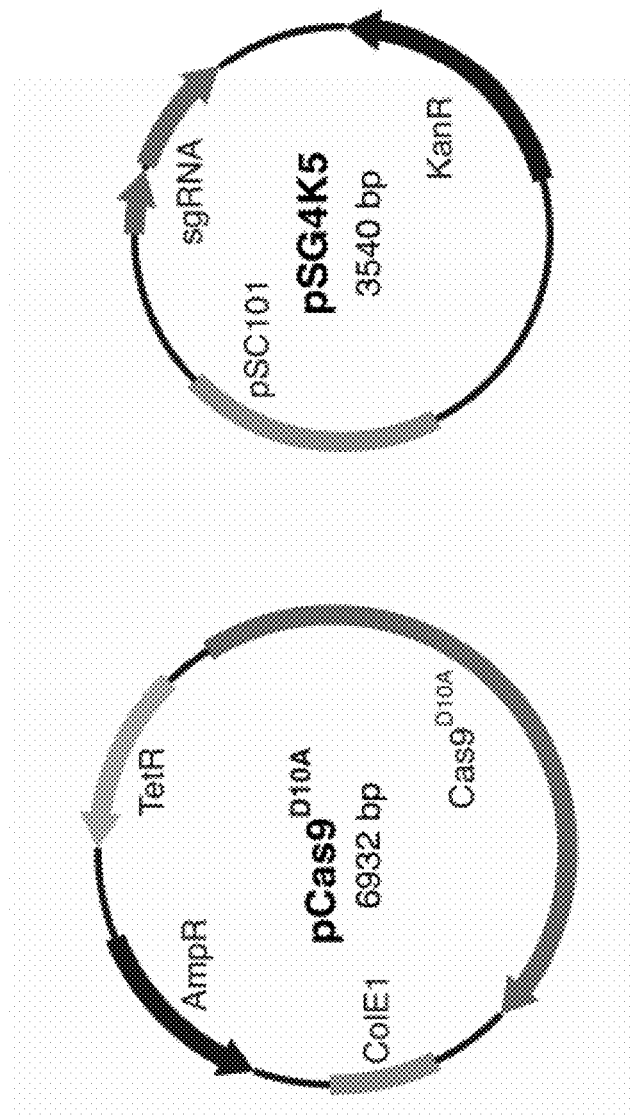
FIGS. 6A and 6B depict the plasmid maps and cloning sites used for nicking CRISPR systems.

3. Construction of Cas9 Mutations pCas9WT was obtained from Addgene (plasmid #44520) (32). pCas9WT contains S. pyogenes wild type Cas9. The plasmid also contains a ColE1 origin of replication, the TetR repressor protein and an ampicillin resistance marker (FIG. 6A). Cas9 D10A and H840A mutations were generated by PCR amplifying 10 pg of pCas9WT using primer pairs 3,4 and 5,6 respectively (Table 1). PCR reactions were purified using GenElute PCR Cleanup Kit (Sigma, #NA1020) following the manufacturer's protocol. DNA was digested with SapI and self-ligated with <40 ng of DNA in 20 µl reactions containing T4 DNA ligase (NEB).

4. Design, Cloning, and Multiplexing of sgRNAs

Figure 6B:
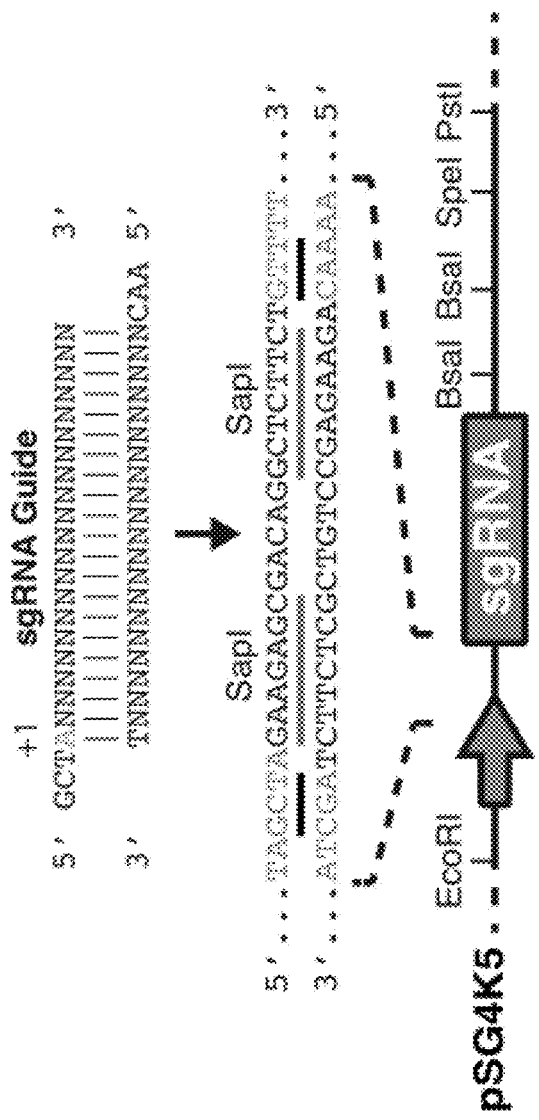

Short Guide RNAs (sgRNAs) were designed by identifying the "NGG" Protospacer Adjacent Motif (PAM) on the noncomplementary strand of the DNA target. 20-21 nucleotides were used as the guide region. sgRNAs contained an Adenine on the 5' end, since A nucleotides functions as effective transcriptional start site. sgRNA guides were synthesized as a pair of 25 nM oligonucleotides (Integrated DNA Technologies, IDT) in a format shown in FIG. 6B. 5' phosphates were added to oligonucleotides by incubating 1 µg of top/bottom oligonucleotides in 50 µl reactions containing 1× T4 DNA Ligase Buffer and 10 units of T4 Polynucleotide Kinase (NEB, #MO201) at 37° C. overnight. Oligonucleotides were duplexed by heating the kinase reactions to 90° C. on an aluminum heating block for 5 minutes followed by slowly returning the reaction to room temperature (25° C.) over approximately 1 hour.

The sgRNA plasmid vector (pSG4K5, SEQ ID NO:30) (FIG. 6A), derived from pSB4K5 (Registry of Standard Biological Parts), was digested with SapI and dephosphorylated using Antarctic Phosphatase (NEB, #MO289) using the manufacture's protocol. 40 ng of SapI digested and dephosphorylated pSG4K5 was ligated to an equimolar amount of sgRNA duplex in 20 µl reactions containing T4

DNA ligase (NEB, #MO202). Multiplex sgRNAs plasmids were constructed by PCR amplifying 10 pg of template plasmid with primers 1 and 2. PCR products were prepared by purifying with GenElute PCR Cleanup Kit, followed by digestion of 500 ng with EcoRI and SpeI (NEB). Reactions were heat inactivated at 80° C. for 20 minutes followed by slowly returning to room temperature. pSG4K5 plasmids containing other guide sequences were digested with BsaI and dephosphorylated using Antarctic Phosphatase. 40 ng of BsaI digested and dephosphorylated pSG4K5 was ligated to an equimolar amount of sgRNA expression cassette in 20 μl reactions containing T4 DNA ligase.

The guide sequences of the sgRNA are listed in Table 2. Guide sequences for sgRNAs where underlined "A" nucleotide corresponds to transcriptional start site (See FIG. 6).

TABLE 2

| sgRNA | Guide Sequeunce | Target |
|---|---|---|
| (-) | AGAAGAGCGACAGGCTCTTCT (SEQ ID NO: 31) | No target, Control sgRNA |
| C1 | ACCATCTAATTCAACAAGAAT (SEQ ID NO: 32) | GFP Coding Sequence |
| T1 | AAAGGAGAAGAACTTTTCAC (SEQ ID NO: 33) | GFP Template Sequence |
| T2 | ACCAATTCTTGTTGAATTAGA (SEQ ID NO: 34) | GFP Template Sequence |
| T3 | ATTCAAGAGTGCCATGCCCGA (SEQ ID NO: 35) | GFP Template Sequence |
| T4 | AGGTATTGATTTTAAAGAAGA (SEQ ID NO: 36) | GFP Template Sequence |
| T5 | ACAACGAAAAGAGAGACCACA (SEQ ID NO: 37) | GFP Template Sequence |
| A | AAATTGTGGTGTTCTAGGGA (SEQ ID NO: 38) | IS5-Histidine Region |
| B | ACACCACAATTTCGCTCTCT (SEQ ID NO: 39) | IS5-Histidine Region |
| C | ACCGGGTAACCACGACCCAGT (SEQ ID NO: 40) | IS5-Histidine Region |
| D | ATGAGAAGTTAAATAACCATG (SEQ ID NO: 41) | IS5-Histidine Region |
| E | ACTCCGAGAATCATAAATACA (SEQ ID NO: 42) | IS5-Histidine Region |
| F | AACTACGCCGATCTGTTGCT (SEQ ID NO: 43) | IS5-Histidine Region |
| G | AATTTTTGTTTTATTAAGGA (SEQ ID NO: 4) | IS5-Histidine Region |
| H | ATTCTGATACGGTTGTTGAT (SEQ ID NO: 45) | IS5-Histidine Region |
| I | ATGGCGACTATGCACTAGGGA (SEQ ID NO: 46) | IS5-Histidine Region |
| J | AGTGCATAGTCGCCACCATTC (SEQ ID NO: 47) | IS5-Histidine Region |
| K | ATTAGCACTTTCCTCTACCAA (SEQ ID NO: 48) | IS5 Tryptophan Region |
| L | ATTATTGTGCATTTCACTAC (SEQ ID NO: 49) | IS5 Tryptophan Region |

5. Transformation of sgRNAs

All strains were made chemically competent using the Z competent *E. coli* Transformation Kit (Zymo Research, #T3002) following the manufacturer's instructions. For transformation of sgRNA expressing pSG4K5, 10 ng of DNA was incubated with 50 μl of competent cell solution for 30 minutes on ice. Samples were heat shocked for 30 seconds in a 42° C. water bath. Samples were then kept on ice for 3 minutes. 300 μl of prewarmed LB media was added and cells were shaken at 37° C. for 1 hour. Following outgrowth, 100 to 300 μl of sample was plated on LB agar containing ampicillin and kanamycin. Plates were incubated overnight. In the case of pooled transformations, following outgrowth for 1 hour, 100 μl of the transformation was added to 5 ml of prewarmed LB liquid medium containing ampicillin and kanamycin. Samples were cultured for 12-14 hours. For fluorescent reporter recombination experiments, samples were analyzed by flow cytometry. For histidine and tryptophan remodeling experiments samples were streak plated or serial diluted onto LB agar plates and/or 5-FOA medium containing appropriate antibiotics.

6. Flow Cytometry

All flow cytometry was conducted on an Accuri C6 How Cytometer (BD Biosciences, CA). Samples were gated by consistent forward scatter (FSC) and side scatter (SSC) and 10,000 events within the FSC/SSC gate were collected. A 488 nm laser excitation and a 530±15 nm emission filter were used for GFP fluorescence determination. Flow cytometry files were analyzed in MatLab (The MathWorks).

7. Fluorescence Microscopy

Colonies picked from sgRNA transformations were cultured for roughly 48 hours in M9 minimal media 0.2% glycerol. Cells were spun down at 5000 g for 2 minutes and washed with 1× Phosphate Buffer Solution (PBS). 2 μl of concentrated cell solution was placed on glass microscope slides and visualized on a Nikon Ti-Eclipse inverted microscope with and LED-based Lumencor SOLA SE Light Engine with appropriate filter sets. GFP was visualized with an excitation at 472 nm and emission at 520/35 nm using a Semrock band pass filter. RFP was visualized with excitation at 562 nm and emission at 641/75 nm. For exposure times and experimental controls see FIG. 8. Constant exposure times, LUT and image gain adjustments were applied to all microscopy data.

8. Remodeling of 36 Kilobase Histidine Genomic Region

The 36 Kb region corresponds to NCBI U00096.3 Positions: 2066159-2102943. sgRNA expression plasmids targeting the IS5-histidine operon region were transformed as described above into K12 *E. coli* expressing Cas9D10A. Pooled transformations were streak plated or serial diluted onto LB agar medium containing ampicillin and kanamycin. Plates were cultured overnight. Individual colonies were randomly selected and replica plated on M9SC and M9-H media. Genomic DNA was prepared from 2 ml of pooled transformation and used for PCR genotyping with primers Ph1-Ph4 (Table 1 #10-13, SEQ ID NOs:10-13).

9. Remodeling of 97 Kilobase Tryptophan Genomic Region

The 97 Kb region corresponds to NCBI U00096.3 Positions: 1299494-1397238. sgRNA expression plasmids targeting the IS5-tryptophan operon region were transformed as described above into K12 MG1655 HK022 (topA, cysB, ribA, fabI), 186 (lapAB) expressing Cas9 D10A. Pooled transformations were grown overnight and plated in serial dilutions on LB agar and LB 5-FOA media. Individual 5-FOA resistant colonies were counted and selected at 24 hours of growth, as colonies tended to grow slowly on 5-FOA plates, furthermore 97 Kb deletions exhibited a slow growth phenotype on LB medium. Selected colonies were replica plated on M9SC and M9-T plates. Genomic DNA was prepared from 2 ml of pooled transformation and used for PCR genotyping with primers Pt1-Pt4 (Table 1 #14-17, SEQ ID NOs:14-17).

To Isolate 133 kilobase, 36 and 97 Kb dual-deletions, tryptophan deletions were regrown overnight in 5 ml LB medium with antibiotics and individual colonies were isolated through serial dilutions and replica plated on M9SC and M9-H medium. We also obtained dual-deletions through histidine deletion screening followed by 5-FOA and tryptophan screening.

10. PCR Genotyping

PCR was conducted on a Bio-Rad C1000 thermocycler with Dual 48/48 Fast Reaction Modules (Bio-Radiations, BioRad). Genomic DNA of cells was prepared with the GenElute Bacterial Genomic DNA Kit (Sigma, #NA2110). Genomic DNA preparations were diluted 100-fold and 1 µl of genomic template was used in 20 µl PCR reactions. PCR reactions contained Phusion DNA Polymerase (NEB, #E0553) and corresponding primers (Table 1). Annealing temperatures and extension times were calculated using the manufacturer's protocol. PCR products were visualized via 1% agarose gel-electrophoresis.

Example 2. CRISPR-Directed Single Stranded DNA Breaks are not Lethal to Prokaryotes To experimentally assess the lethality of CRISPR-directed SSBs in wild type *E. coli*, we constructed a two-plasmid system (FIG. 6A): one plasmid expresses Cas9 and another expresses an sgRNA against a genome integrated green fluorescent protein (GFP) gene (FIG. 1A). Multiple mutant versions of Cas9, including Cas9D10A, Cas9H840A, and a Cas9D10A, H840A double mutant (29), were tested. The D10A mutation abrogates function of the RuvCI nuclease domain, generating a Cas9 capable of only nicking the DNA strand complimentary to the sgRNA. On the other hand, the H840A mutation removes function of the HNH nuclease domain resulting in a Cas9 that cleaves only the non-complimentary strand to the sgRNA (FIG. 1A) (29). Combination of both D10A and H840A leaves Cas9 catalytically dead (dCas9) (32). Therefore, dCas9 can only bind to target DNA without any cleavage of the chromosome.

Figure 1B:
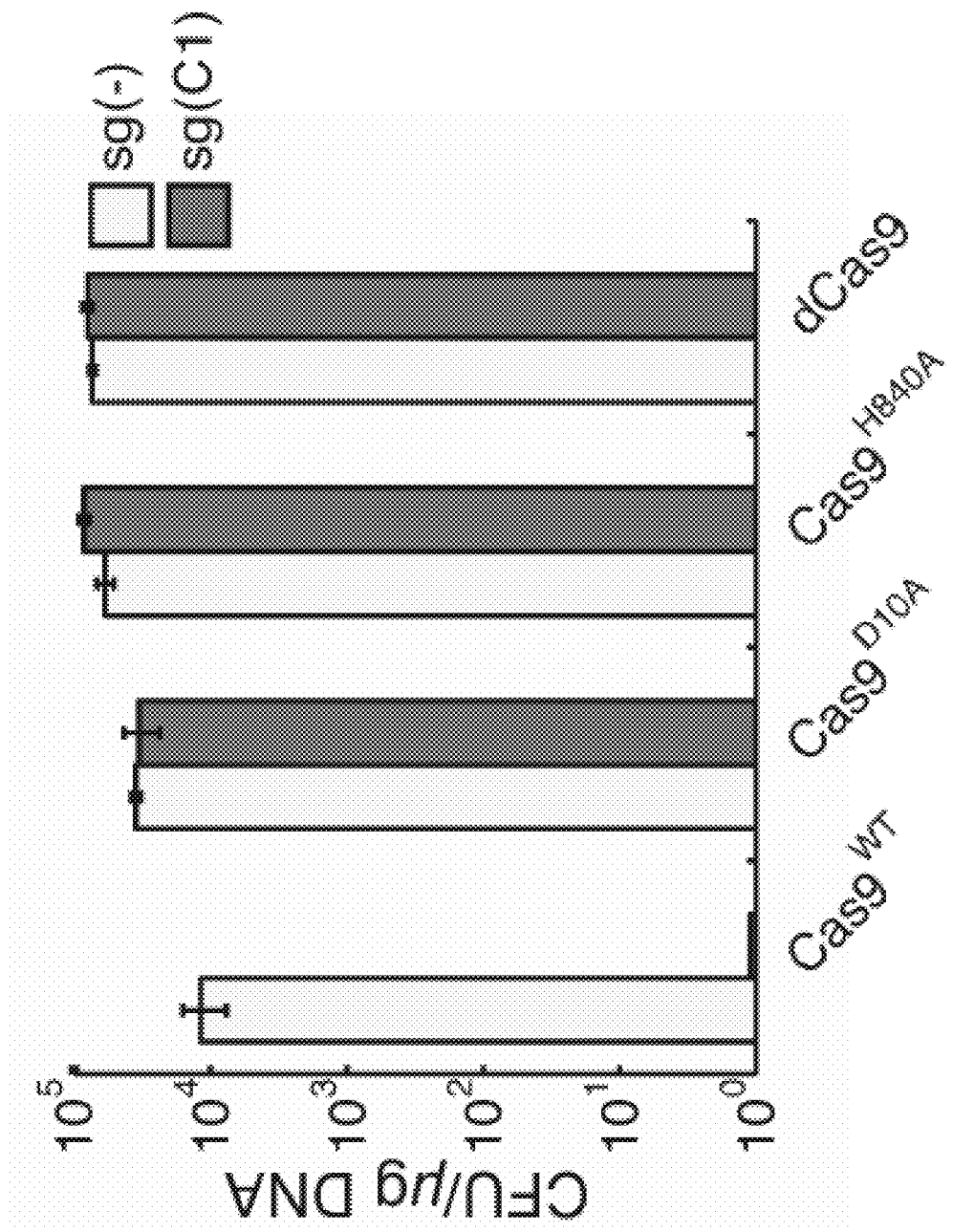
Figure 7A:
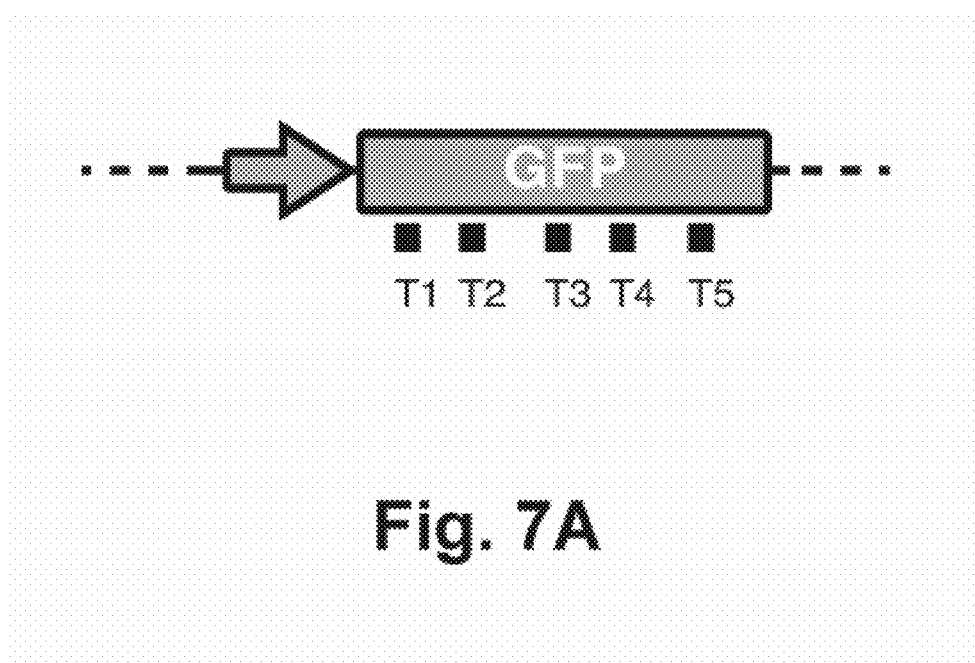
FIGS. 7A and 7B depict experimental comparison of multiple GFP targeting sgRNAs.
Figure 7B:
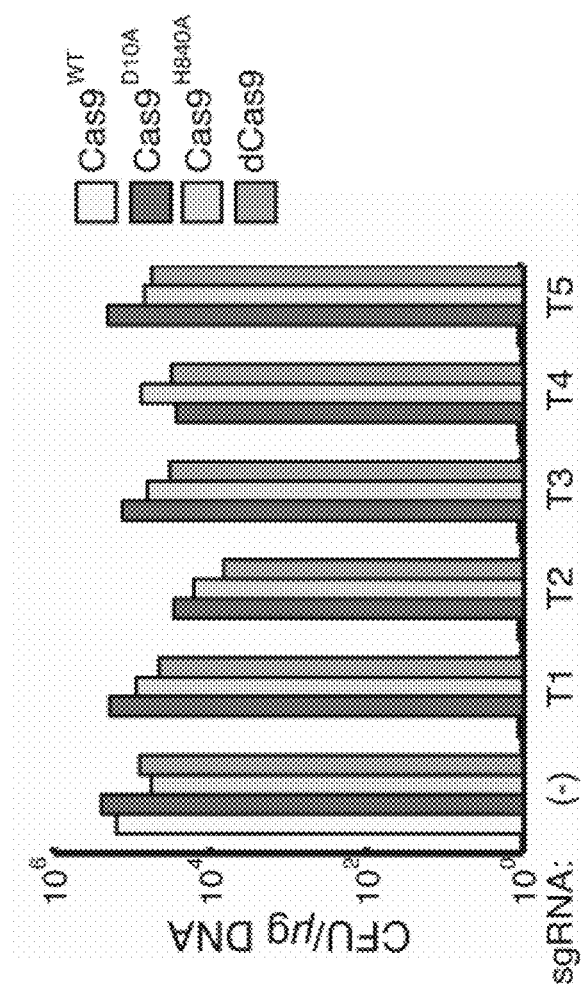

We transformed GFP targeting sgRNA, sg(C1), into *E. coli* K12 coexpressing the aforementioned Cas9 variants and compared resulting colonies to a control non-targeting sgRNA, sg(-). As can be seen in FIG. 1B, sgRNA targeting GFP showed no viable colony forming units when wild type Cas9 (Cas9WT) was expressed, while nicking or catalytically inactive variants of Cas9 don't affect viability. This suggests that CRISPR induced DSBs are lethal to *E. coli* cells while CRISPR induced SSBs have no severe impact on viability. It is also demonstrated that such impacts are not cleavage position dependent (FIG. 7B).

Figure 2A:
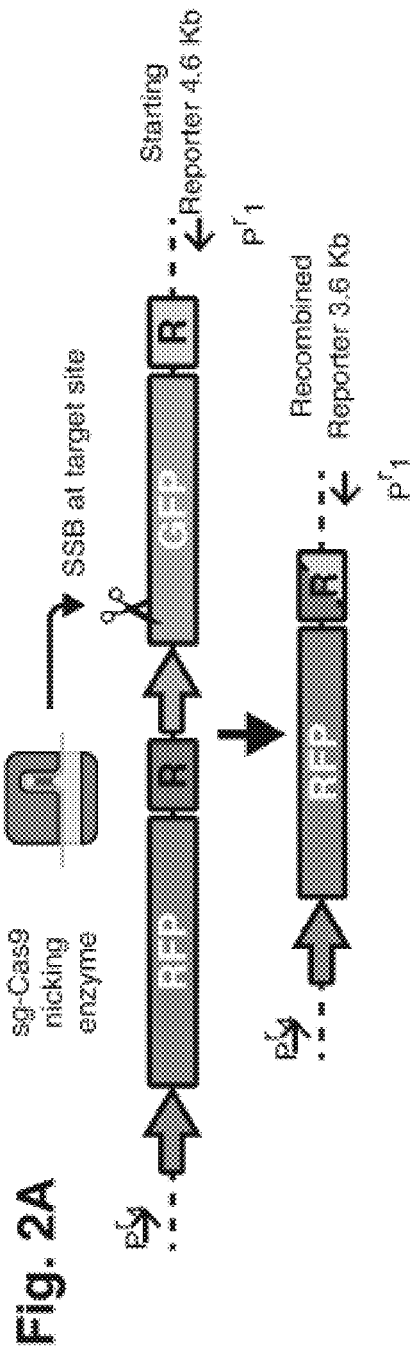
FIGS. 2A-2E show that nick-induced recombination leads to single gene chromosomal deletion.

Example 3. Genome Deletion in Prokaryotes Using the CRISPR-Cas9 System of the Invention 1. Proof of Principle Although it has been reported that HR could be an inconvenience in building synthetic gene circuits with repetitive parts (33), a precise nick between repeat sequences could hypothetically induce rationally designed HR to achieve targeted genome deletion (34). To explore the potential of using CRISPR generated nicking to induce targeted HR, we constructed a genome integrated synthetic dual-reporter system (FIG. 2A) to query gene deletion and viability. In this system, GFP was designed to be flanked by two 129 base pair direct repeats (R). We systematically targeted nicking sites between direct repeats to both strands of GFP with Cas9D10A and Cas9H840A. The fluorescent population distributions of sgRNA(T1) Cas9D10A indicate that GFP is phenotypically lost in 86% of the cells (FIG. 2B, outlined). This target site is about 110 bp away from the left repeat.

Figure 8:
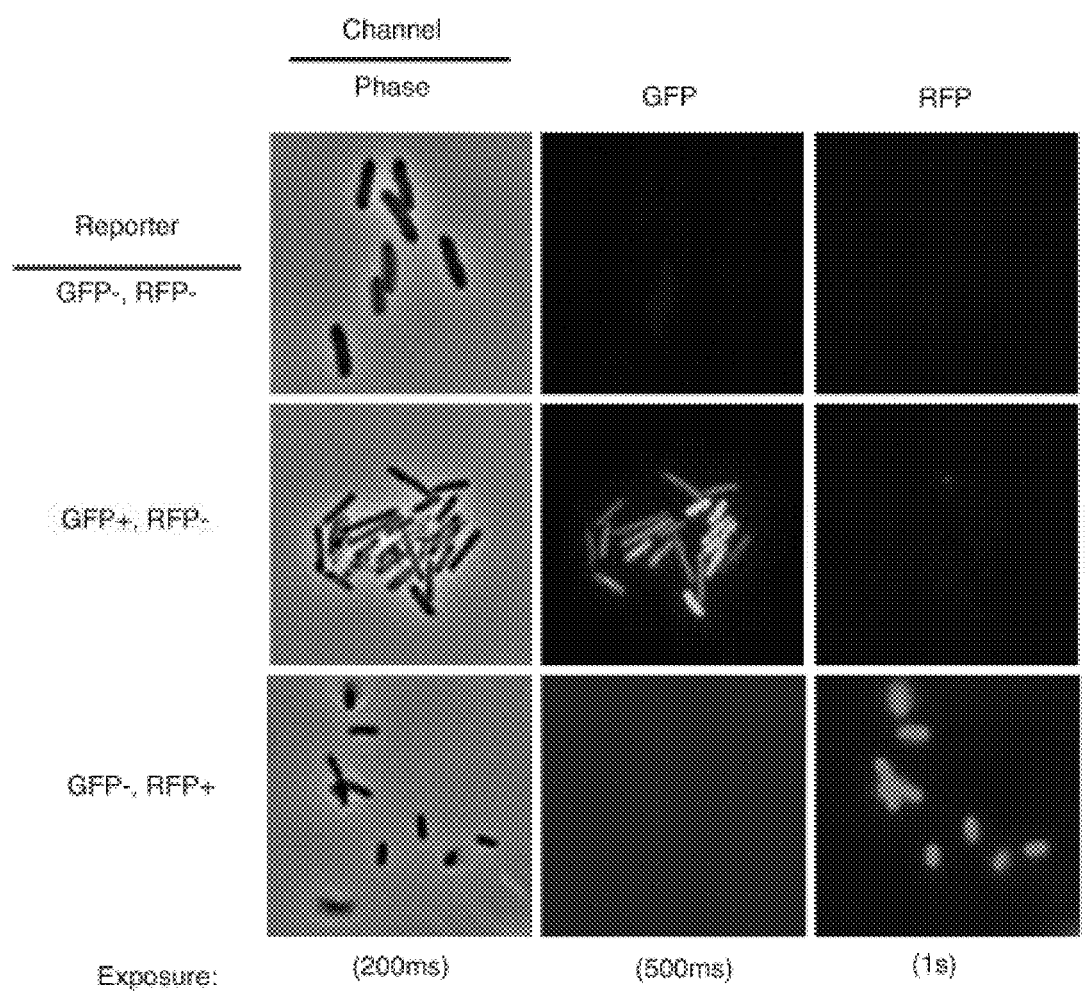
FIG. 8 shows that the fluorescence signal by microscopy is not due to auto-fluorescence or reporter overlap. Different combinations of genome integrated reporters are visualized as described in Methods. Exposure times are listed below images. Constant exposure times, LUT, and image gain adjustments were applied to all microscopy data.
Figure 9:
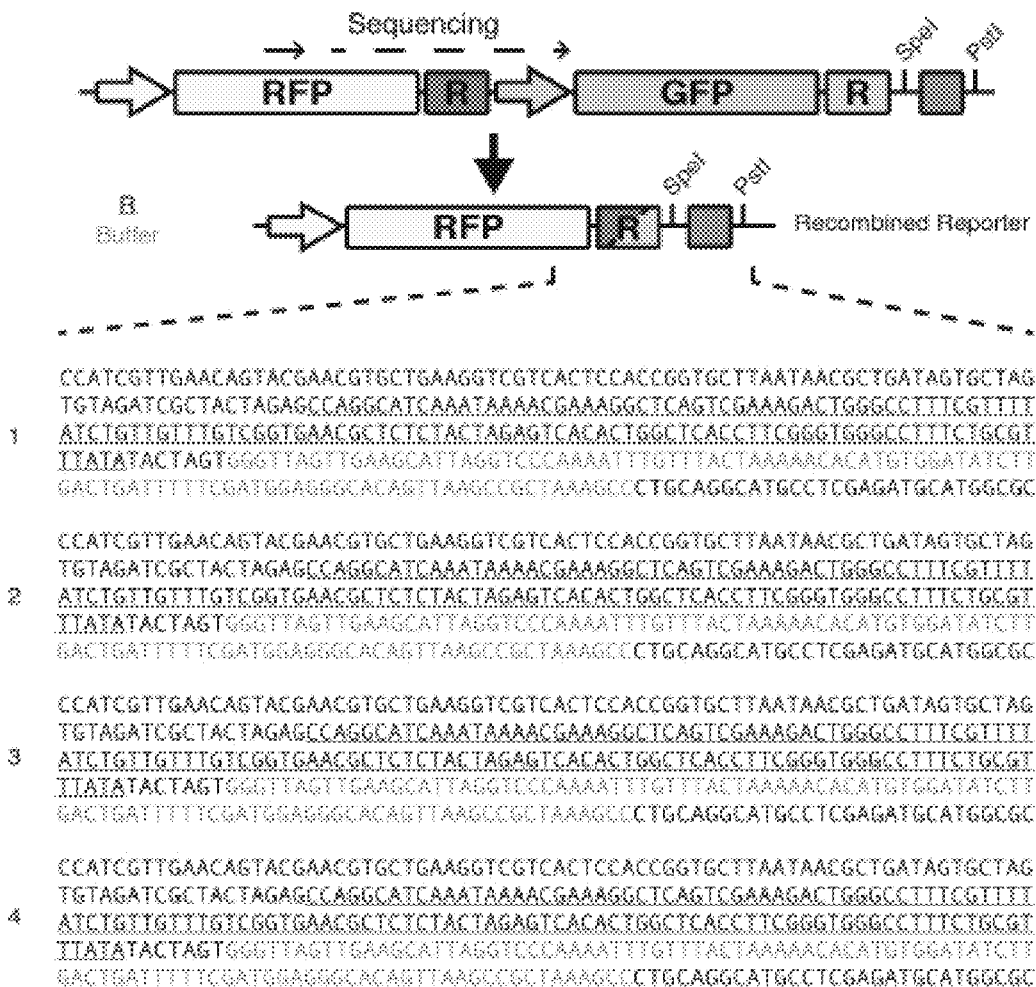
FIG. 9 depicts the confirmation of fluorescent reporter recombination by DNA sequencing. A schematic representation of the chromosomally integrated dual fluorescence reporter employed for homologous recombination experiments. The arrow represents the sequencing primer (primer #9, Table 1) with the dashed line indicating the direction of the Sanger sequencing read. Sequence landmarks are indicated by label. Homologous repeats (R), SpeI and PstI restriction sites and an arbitrary buffer sequence in between restriction sites. Results for 4 separate sequencing samples. Repeat sequences is underlined and the buffer sequence is light gray. The absence of GFP sequence and the detection of the buffer sequence indicate formation of the recombined directed repeats.
Figure 10A:
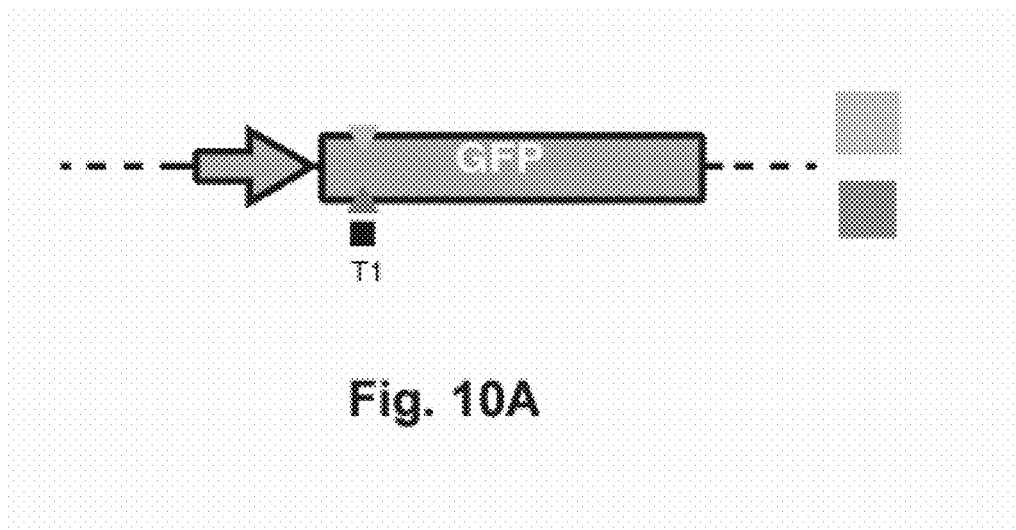
FIGS. 10A and 10B show flow cytometry analysis of GFP deletion without homologous repeats on both ends of the gene.
Figure 10B:
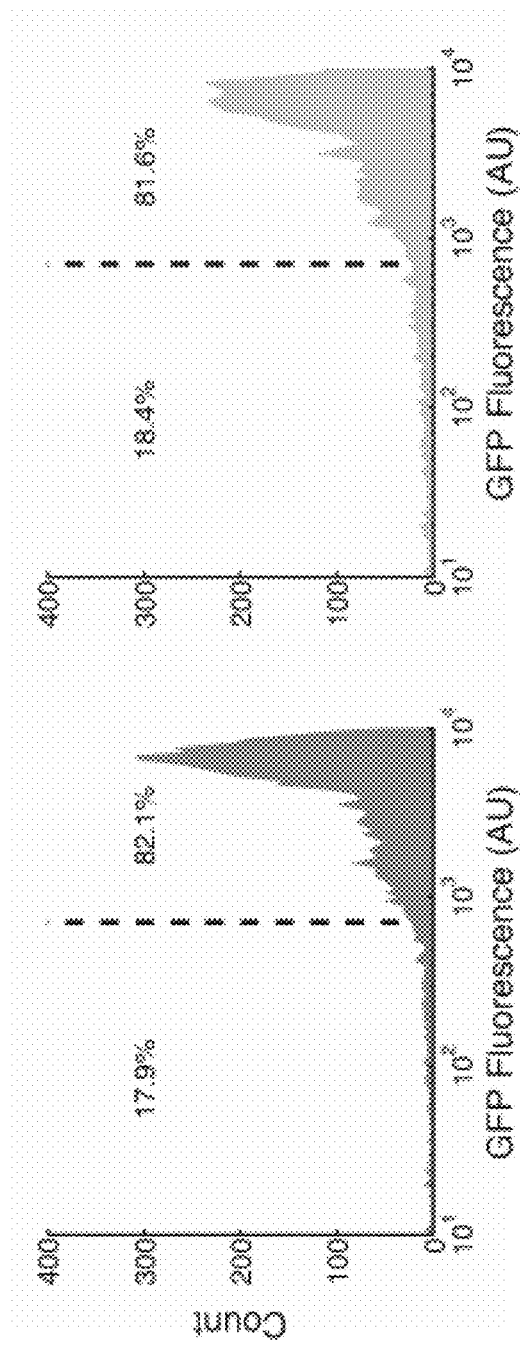

To verify HR as the cause of GFP signal loss, individual colonies were obtained from transformations for further analysis. Fluorescence microscope images show that, when targeted by sgRNA(T1) and Cas9D10A, cells grow normally and GFP fluorescence is undetectable while RFP signal is intact (FIG. 2D, bottom), which is not the result of autofluorescence (FIG. 8). This ruled out cell death as the cause of diminished GFP signal. Gel-electrophoresis results also verified a GFP knockout due to HR (FIG. 2E). Sanger sequencing of the PCR products further confirmed that recombination indeed occurred between the two direct repeats (FIG. 9).

Figure 2C:
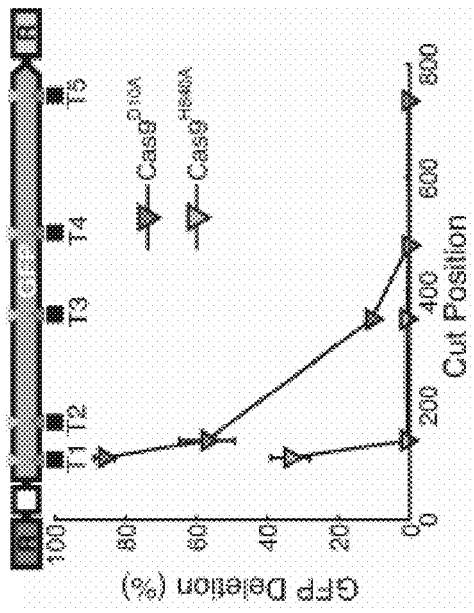
Figure 2B:
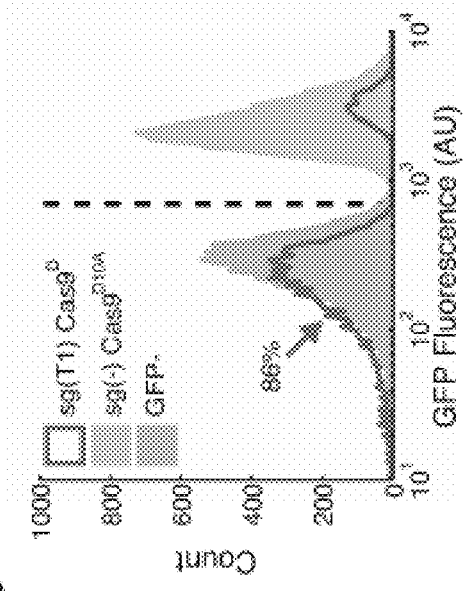
Figure 2E:
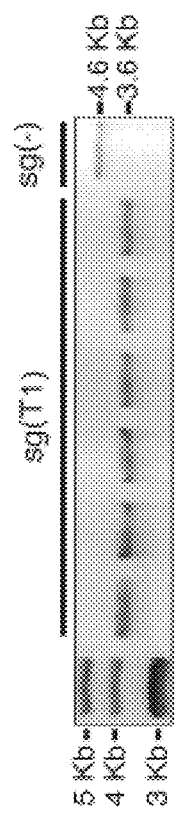
Figure 2D:
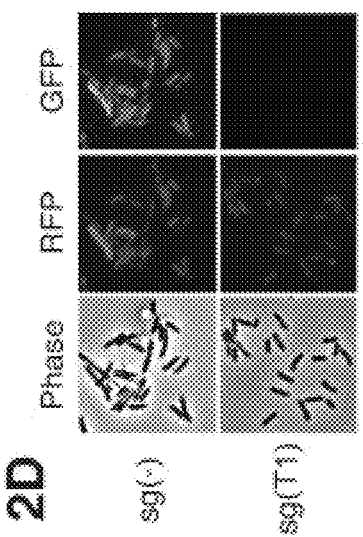

It is interesting to see that the percentage of GFP negative cells quickly decreases as the target site is moved further away from the left repeat (FIG. 2C, dark gray triangles). However, such a loss of GFP fluorescence is less pronounced when Cas9H840A is used to nick the opposite strand (FIG. 2C). This suggests a strong strand and position dependency of single-nick induced local-homologous recombination. Finally, without the presence of two direct repeats on each end of GFP, neither Cas9D10A nor Cas9H840A can induce targeted GFP fluorescence abolishment (FIG. 9). Taken together, our results show that chromosomally targeted Cas9D10A can induce targeted SSBs to capacitate recombination between homologous sequences.

2. 36 kb Histidine Genome Deletion

Figure 3A:
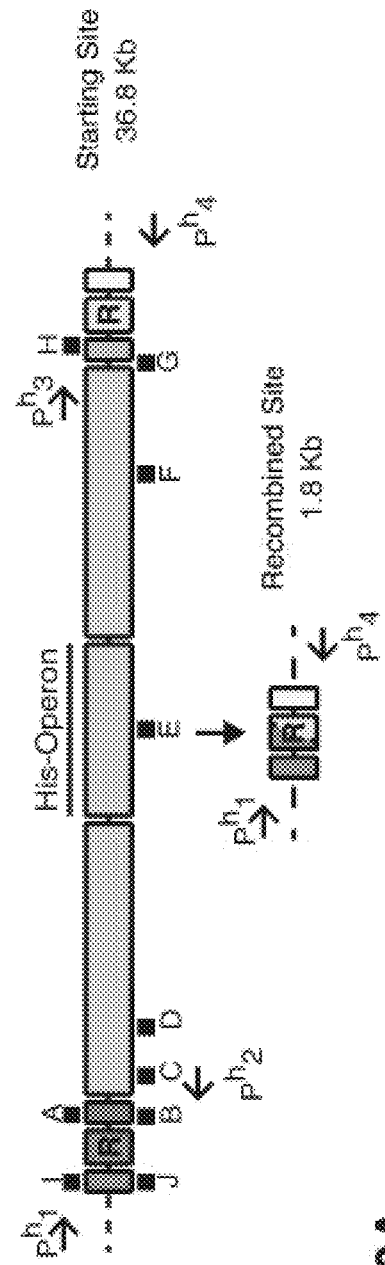
FIGS. 3A-3E show that nickase directed deletion of a 36 kilobase genomic region.

To investigate how CRISPR-directed SSBs can be applied to remodel large sections of genome in *E. coli*, we designed sgRNAs to target insertion sequences (IS) in direct repeat orientations and tested for genome deletion. Widespread distributions of transposable DNAs, such as IS elements, have been implicated to be responsible for large genomic changes (1, 35), but also provide a rich source of repetitive sequences to apply our method. We identified a region with two IS5 elements 35 Kb apart. The DNA flanked by IS5 (FIG. 3A). The His operon provides us a convenient screenable marker for deletions. Cells containing the His operon are histidine prototrophs. When deleted, the *E. coli* is converted to a histidine auxotroph (unable to grow without provision of the amino acid).

Figure 3B:
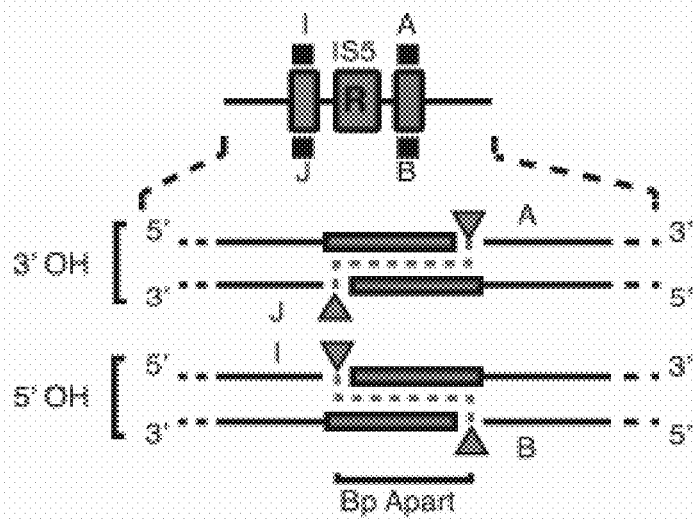
Figure 3C:
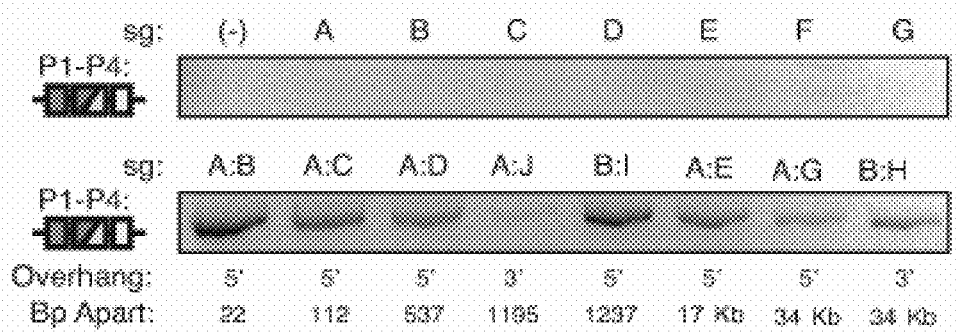

To employ single-stranded lesions to direct recombination across the Histidine biosynthetic region, we systematically targeted a series of 10 sgRNAs (sgA-J) in the vicinity of the two IS5 sequences. These included targets directly adjacent to the repeats (R) on both strands along with multiple target sites within the 36.8 Kb region (FIG. 3A). We transformed K12 *E. coli* expressing nicking Cas9D10A with plasmids expressing individual and paired sgRNA combinations and cultured in pooled transformations. We employed a PCR based approach to monitor recombination between repeats. Interestingly, the recombined site was undetectable in single targeting versions, unlike what's shown above for GFP deletion. This indicates individual single-strand breaks are insufficient to direct HR across large regions (FIG. 3C). When employing paired sgRNA, formation of the deletion product was detectable for multiple combinations (FIG. 3C). In particular, sgRNAs targeting adjacent to each other, sg(A:B), and across the repetitive sequences, sg(B:I), had prominently undergone recombination (FIGS. 3B and 3C).

Figure 3D:
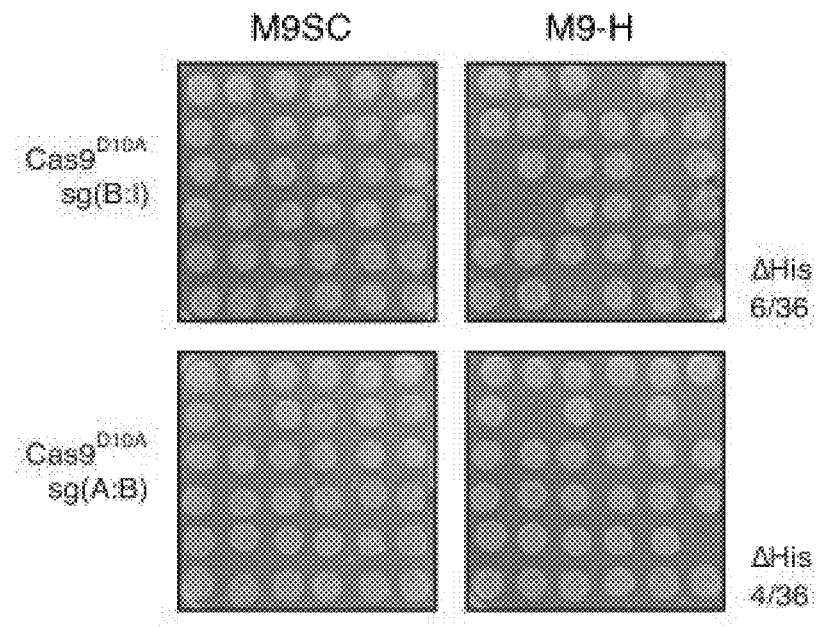
Figure 3E:
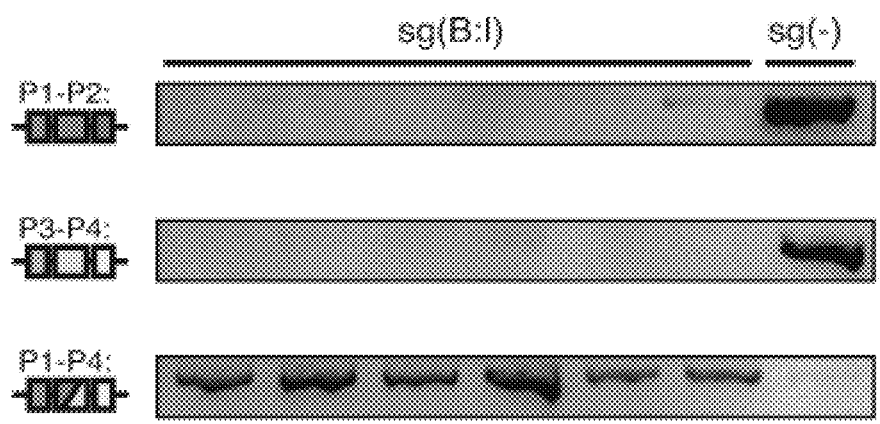
Figure 11:
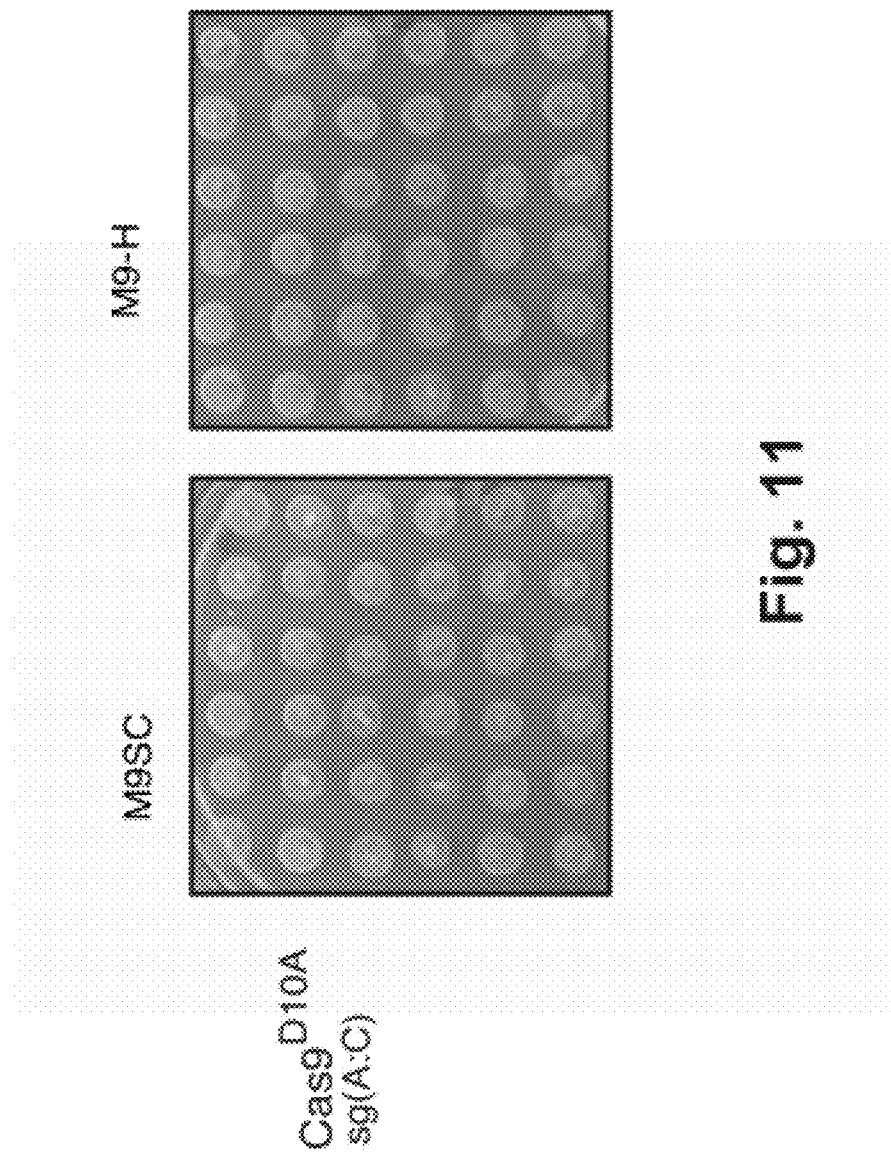
FIG. 11 shows auxotrophy screening of sg(A:C). Replica plates sg(A:C) colonies on M9 synthetic complete (M9SC) and M9 without histidine (M9-H). There are no easily obtainable histidine deletions (<1/36) when cut sites are located farther apart.

Individual colonies were then isolated from transformations and subjected to random screening for histidine auxotrophy. Our results show that sgRNAs generating a 5' overhangs across the repeat sequence, sg(B:I), and sgRNAs targeting in close proximity to each other, sg(A:B), have roughly 17% and 11% success rate of 36 Kb deletion, respectively (FIGS. 3B and 3D). Other paired-nicking transformations with faint banding (e.g. sg(A:C)) were screened and confirm the absence of histidine deletions (FIG. 11). Finally, we confirmed that histidine auxotrophs consistently harbor the expected deletion by using multiple primer sets querying the presence of starting and recombined junctions (FIG. 3E). These results show that dual-targeted nicking systems can effectively induce recombination across 36 Kb with efficiencies approaching 20 percent of a bacterial population.

The high efficacy of sg(B:I) provided us with design principles for further implementation of nicking-directed recombination devices. sgRNAs should be targeted adjacent to both ends of a repetitive sequence with Cas9D10A cut sites within close proximity (approximately 22 nucleotides) of the homology. The left sgRNA is complimentary the top strand and the right guide to the bottom DNA strand. This results in a 5' overhang cleavage orientation. Interestingly, the requisite for a 5' cut orientation is consistent with previously reported application of double nicking systems in mammalian cells 30.

3. Multiplex Remodeling Achieves 133 Kb Deletion

Figure 4A:
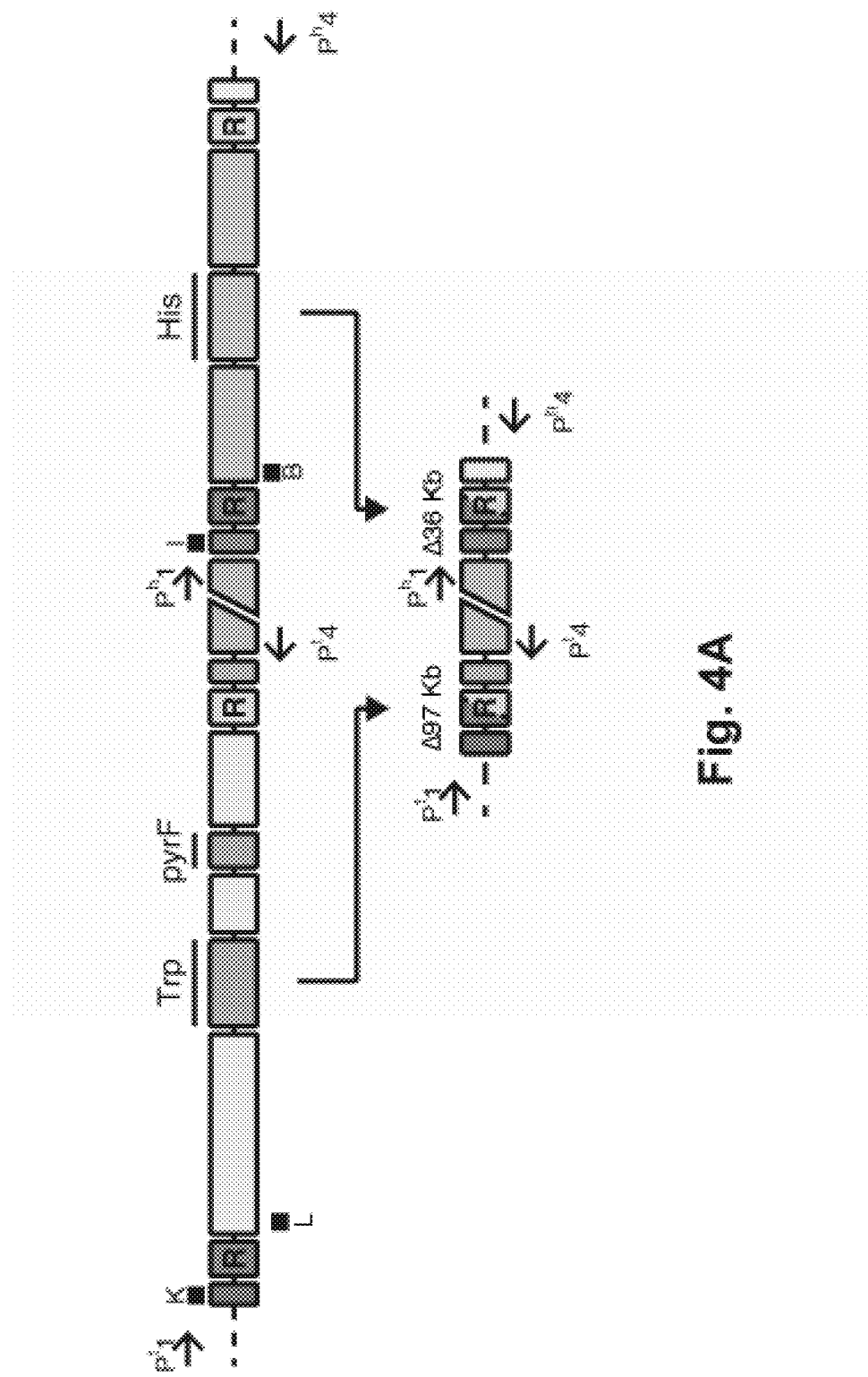
FIGS. 4A-4C show that a multiplex targeted genome remodeling can delete 133 Kb from the genome of a bacteria.

To further explore the potential of our method to direct multiplexed large-scale genomic recombination, we identified a 97 Kb genomic region with the tryptophan biosynthesis operon (TRP) and the pyrF gene flanked by repeats (FIG. 4A). This region enables screening for deletion by testing for tryptophan auxotrophy along with positive selection of deletion using 5-Fluoroorotic Acid (5-FOA) (36). A special strain was created with duplicate copies of essential genes found within the 97 Kb section of genome integrated into separate loci. This alleviated the essentiality of the region and enabled nickase-directed remodeling.

Figure 4B:
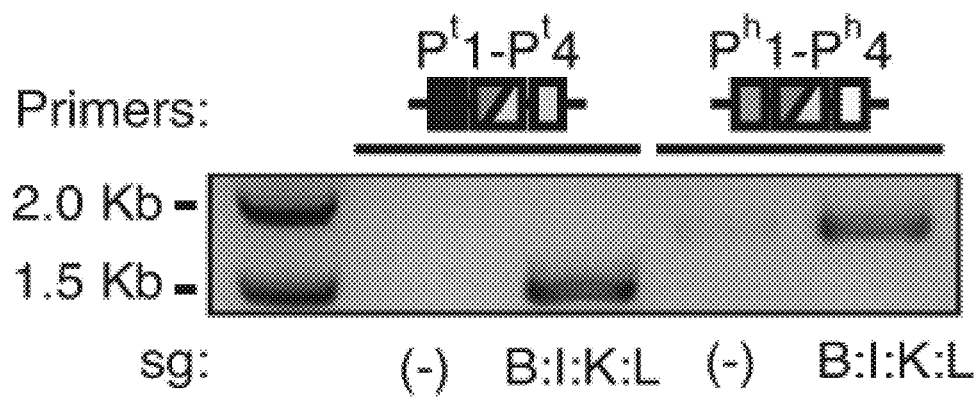
Figure 4C:
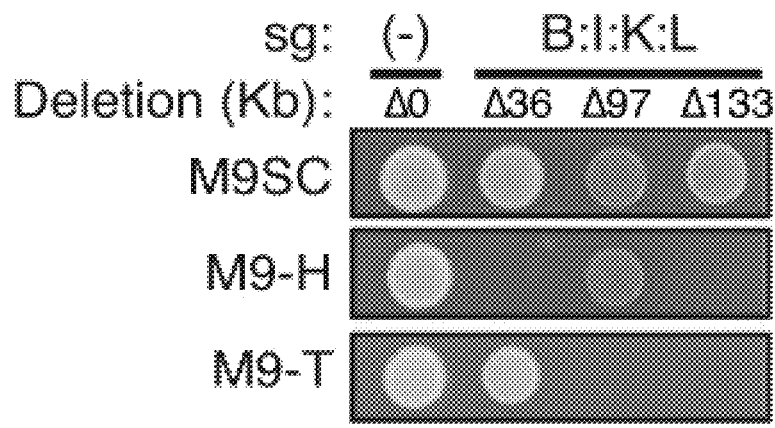
Figure 12A:
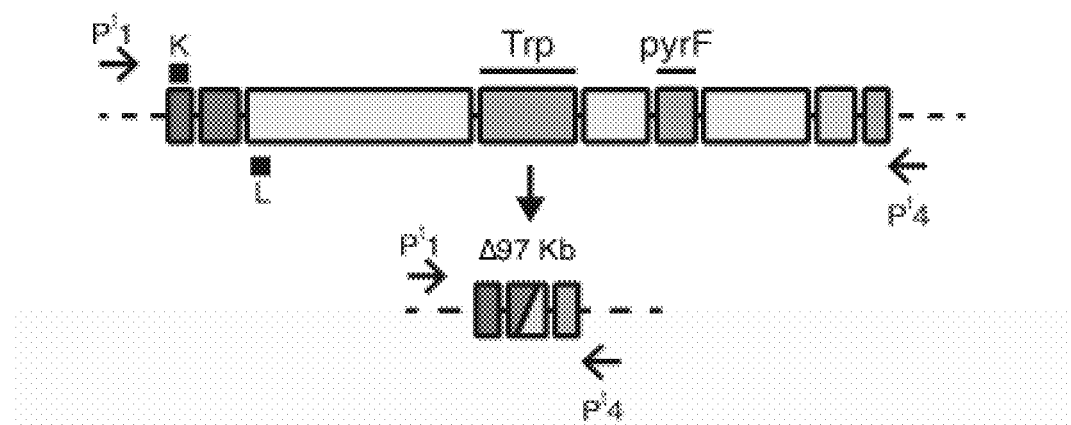
FIGS. 12A-12D depict the characterization of nicking directed deletion of 97 Kb.
Figure 12B:
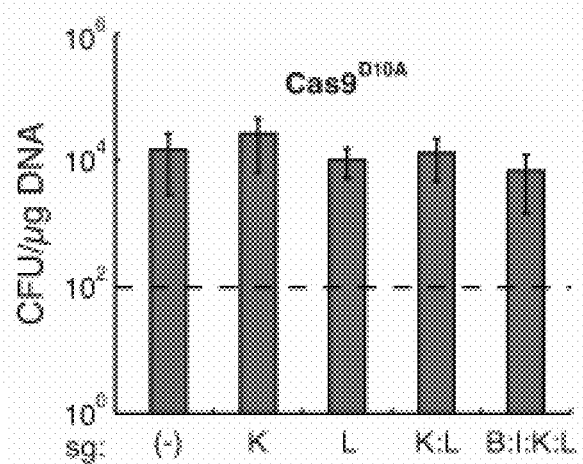
Figure 12C:
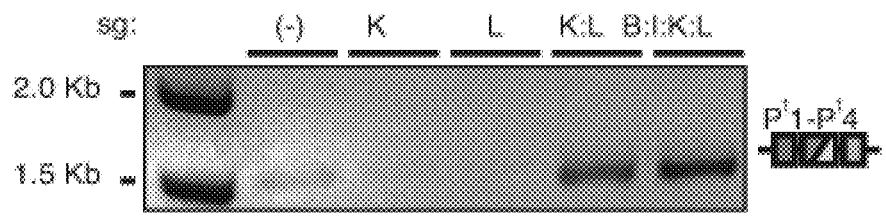
Figure 12D:
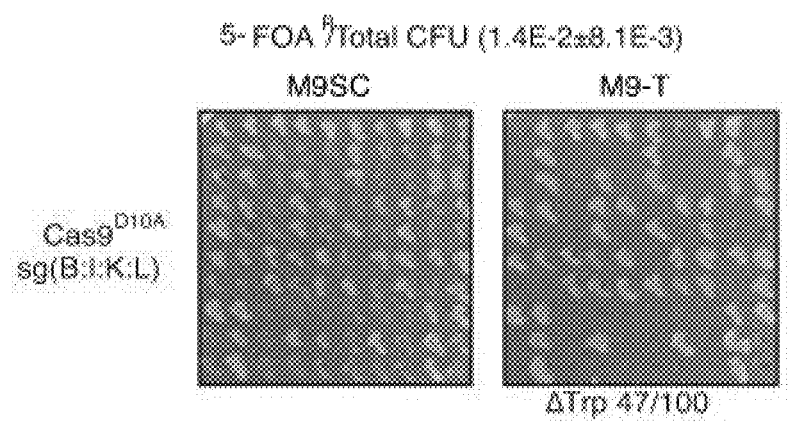

To multiplex target the 97 Kb genomic region along with the 36 Kb region tested, we applied principles of dual sgRNA design from above experiments. sgRNAs K and L were designed and coupled to the previously employed guides B and I. This generated a four-target CRISPR system, sg(B:I:K:L), which should direct multiplex remodeling of the *E. coli* genome (FIG. 4A). We validated the necessity of cooperative nicking to induce homologous recombination and determined that four-targeted nicking did not substantially reduce transformation efficiency (FIG. 12B). In pooled transformations of the multi-targeted CRISPR device, we detected recombination at both His and Trp regions (FIG. 4B). This indicated that HR at both sites was simultaneously occurring within the population of cells. To quantify the 97 Kb deletion we combined results for 5-FOA and TRP markers. 47% of the 5-FOA resistant colonies exhibited clear tryptophan auxotrophy (FIG. 12D). Combining results for both markers, we estimated deletion efficiency to be 7±4 deletions per 1000 cells. After initial 5-FOA/TRP screens we further tested for histidine deletion. Using stepwise screening we reliably obtained 36 kb, 97 kb single and 133 kb dual-deletions from sg(B:I:K:L) transformations (FIG. 4C), indicating successful deletion of 133 Kb of *E. coli* genome using our approach. Thus a 3% reduction of *E. coli* genome was achieved with only one plasmid transformation. These results verify the dual-targeted sgRNA design for directed recombination. Likewise, the results exemplify the potential of multiplex CRISPR-guided nicking devices to remodel large genomic regions.

Example 4. Genome Replacement in Prokaryotes Using the CRISPR-Cas9 System of the Invention Targeted gene replacement using the CRISPR-Cas9 system of the invention requires the use of donor vectors comprising homologous sequences that flank a replacement sequence (payload sequence) (FIG. 5). The homologous sequences may be repeated sequences in the bacterial genome or they may be sequences that are homologous to the portions of bacterial genome. CRISPR targeted nicking stimulates recombination between prokaryotic genome and the vector containing the homologous sequences. The identity of the homologous sequences determines the location of gene replacement and the replacement sequence (or payload sequence) determines what is inserted in place of the original target gene. The methods of designing donor sequences and placing them along with the replacement sequence in a plasmid vector are known to those having ordinary skill in the art.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

1. Raeside, C. et al. Large chromosomal rearrangements during a long-term evolution experiment with *Escherichia coli*. mBio 5, e01377-01314 (2014).
2. Barrick, J. E. et al. Genome evolution and adaptation in a long-term experiment with *Escherichia coli*. Nature 461, 1243-1247 (2009).
3. Darling, A. E., Miklos, I. & Ragan, M. A. Dynamics of Genome Rearrangement in Bacterial Populations. PLoS Genet. 4, (2008).
4. Gong, W. et al. Engineering microbes for efficient production of chemicals. (2012). at <http://www.google.com/patents/US20120220000>
5. Cooper, V. S., Schneider, D., Blot, M. & Lenski, R. E. Mechanisms causing rapid and parallel losses of ribose catabolism in evolving populations of *Escherichia coli* B. J. Bacteriol. 183, 2834-2841 (2001).
6. Riehle, M. M., Bennett, A. F. & Long, A. D. Genetic architecture of thermal adaptation in *Escherichia coli*. Proc. Natl. Acad. Sci. U.S.A 98, 525-530 (2001).

7. Enyeart, P. J. et al. Generalized bacterial genome editing using mobile group II introns and Cre-lox. Mol. Syst. Biol. 9, (2013).
8. Kolisnychenko, V. et al. Engineering a Reduced *Escherichia coli* Genome. Genome Res. 12, 640-647 (2002).
9. Cong, L. et al. Multiplex Genome Engineering Using CRISPR/Cas Systems. Science 339, 819-823 (2013).
11. Jiang, W., Bikard, D., Cox, D., Zhang, F. & Marraffini, L. A. RNA-guided editing of bacterial genomes using CRISPR-Cas systems. Nat. Biotechnol. 31, 233-239 (2013).
12. Makarova, K. S. et al. Evolution and classification of the CRISPR-Cas systems. Nat. Rev. Microbiol. 9, 467-477 (2011).
13. Barrangou, R. et al. CRISPR Provides Acquired Resistance Against Viruses in Prokaryotes. Science 315, 1709-1712 (2007).
14. Marraffini, L. A. & Sontheimer, E. J. CRISPR Interference Limits Horizontal Gene Transfer in Staphylococci by Targeting DNA. Science 322, 1843-1845 (2008).
15. Sapranauskas, R. et al. The *Streptococcus thermophilus* CRISPR/Cas system provides immunity in *Escherichia coli*. Nucleic Acids Res. 39, 9275-9282 (2011).
16. Mojica, F. J. M., Diez-Villasenor, C., Garcia-Martinez, J. & Almendros, C. Short motif sequences determine the targets of the prokaryotic CRISPR defence system. Microbiology 155, 733-740 (2009).
17. Marraffini, L. A. & Sontheimer, E. J. Self versus non-self discrimination during CRISPR RNA-directed immunity. Nature 463, 568-571 (2010).
18. Citorik, R. J., Mimee, M. & Lu, T. K. Sequence-specific antimicrobials using efficiently delivered RNA-guided nucleases. Nat Biotech 32, 1141-1145 (2014).
19. Caliando, B. J. & Voigt, C. A. Targeted DNA degradation using a CRISPR device stably carried in the host genome. Nat Commun 6, (2015).
20. Edgar, R. & Qimron, U. The *Escherichia coli* CRISPR system protects from λ lysogenization, lysogens, and prophage induction. J. Bacteriol. 192, 6291-6294 (2010).
21. Vercoe, R. B. et al. Cytotoxic Chromosomal Targeting by CRISPR/Cas Systems Can Reshape Bacterial Genomes and Expel or Remodel Pathogenicity Islands. PLoS Genet 9, e1003454 (2013).
22. Oh, J.-H. & Pijkeren, J.-P. van. CRISPR-Cas9-assisted recombineering in *Lactobacillus reuteri*. Nucleic Acids Res. gku623 (2014). doi:10.1093/nar/gku623
23. Sharan, S. K., Thomason, L. C., Kuznetsov, S. G. & Court, D. L. Recombineering: a homologous recombination-based method of genetic engineering. Nat. Protoc. 4, 206-223 (2009).
24. Mosberg, J. A., Lajoie, M. J. & Church, G. M. Lambda red recombineering in *Escherichia coli* occurs through a fully single-stranded intermediate. Genetics 186, 791-799 (2010).
25. Wang, H. H. et al. Programming cells by multiplex genome engineering and accelerated evolution. Nature 460, 894-898 (2009).
26. Isaacs, F. J. et al. Precise Manipulation of Chromosomes in Vivo Enables Genome-Wide Codon Replacement. Science 333, 348-353 (2011).
27. Datsenko, K. A. & Wanner, B. L. One-step inactivation of chromosomal genes in *Escherichia coli* K-12 using PCR products. Proc. Natl. Acad. Sci. 97, 6640-6645 (2000).
28. Baba, T. et al. Construction of *Escherichia coli* K 12 in frame, single gene knockout mutants: the Keio collection. Mol. Syst. Biol. 2, (2006).
29. Jinek, M. et al. A Programmable Dual-RNA-Guided DNA Endonuclease in Adaptive Bacterial Immunity. Science 337, 816-821 (2012).
30. Ran, F. A. et al. Double Nicking by RNA-Guided CRISPR Cas9 for Enhanced Genome Editing Specificity. Cell 155, 479-480 (2013).
31. *Mali*, P. et al. CAS9 transcriptional activators for target specificity screening and paired nickases for cooperative genome engineering. Nat. Biotechnol. 31, 833-838 (2013).
32. Qi, L. S. et al. Repurposing CRISPR as an RNA-Guided Platform for Sequence-Specific Control of Gene Expression. Cell 152, 1173-1183 (2013).
33. Chen, Y.-J. et al. Characterization of 582 natural and synthetic terminators and quantification of their design constraints. Nat. Methods 10, 659-664 (2013).
34. Lovett, S. T., Drapkin, P. T., Sutera-Jr., V. A. & Gluckman-Peskind, T. J. A Sister-Strand Exchange Mechanism for Reca-Independent Deletion of Repeated DNA Sequences in *Escherichia Coli*. Genetics 135, 631-642 (1993).
35. Shapiro, J. A. Letting *Escherichia coli* Teach Me About Genome Engineering. Genetics 183, 1205-1214 (2009).
36. Redder, P. & Linder, P. New Range of Vectors with a Stringent 5-Huoroorotic Acid-Based Counterselection System for Generating Mutants by Allelic Replacement in *Staphylococcus aureus*. Appl. Environ. Microbiol. 78, 3846-3854 (2012).
37. Way, J. C., Collins, J. J., Keasling, J. D. & Silver, P. A. Integrating Biological Redesign: Where Synthetic Biology Came From and Where It Needs to Go. Cell 157, 151-161 (2014).
38. Pál, C., Papp, B. & Pósfai, G. The dawn of evolutionary genome engineering. Nat. Rev. Genet. 15, 504-512 (2014).
39. Lu, T. K., Khalil, A. S. & Collins, J. J. Next-generation synthetic gene networks. Nat. Biotechnol. 27, 1139-1150 (2009).
40. Mishra, D., Rivera, P. M., Lin, A., Del Vecchio, D. & Weiss, R. A load driver device for engineering modularity in biological networks. Nat. Biotechnol. 32, 1268-1275 (2014).
41. Hacker, J., Blum-Oehler, G., Mühldorfer, I. & Tschäpe, H. Pathogenicity islands of virulent bacteria: structure, function and impact on microbial evolution. Mol. Microbiol. 23, 1089-1097 (1997).
42. Lu, T. K. & Collins, J. J. Engineered bacteriophage targeting gene networks as adjuvants for antibiotic therapy. Proc. Natl. Acad. Sci. 106, 4629-4634 (2009).
43. Farzadfard, F. & Lu, T. K. Genomically encoded analog memory with precise in vivo DNA writing in living cell populations. Science 346, 1256272 (2014).
44. Ellis, T., Wang, X. & Collins, J. J. Diversity-based, model-guided construction of synthetic gene networks with predicted functions. Nat. Biotechnol. 27, 465-471 (2009).
45. Litcofsky, K. D., Afeyan, R. B., Krom, R. J., Khalil, A. S. & Collins, J. J. Iterative plug-and-play methodology for constructing and modifying synthetic gene networks. Nat. Methods 9, 1077-1080 (2012).
46. Stricker, J. et al. A fast, robust and tunable synthetic gene oscillator. Nature 456, 516-519 (2008).
47. Payne, S. et al. Temporal control of self organized pattern formation without morphogen gradients in bacteria. Mol. Syst. Biol. 9, 697 (2013).
48. Wu, M. et al. Engineering of regulated stochastic cell fate determination. Proc. Natl. Acad. Sci. 201305423 (2013). doi:10.1073/pnas.1305423110

49. St-Pierre, F. et al. One-Step Cloning and Chromosomal Integration of DNA. ACS Synth. Biol. 2, 537-541 (2013).

50. Mahalakshmi, S., Sunayana, M. R., SaiSree, L. & Reddy, M. yciM is an essential gene required for regulation of lipopolysaccharide synthesis in *Escherichia coli*. Mol. Microbiol. 91, 145-157 (2014).

```
pSG4K5 (3540 bp)
J23119 Promoter, Transcriptional Start, Inverted
SapI sites, sgRNA Hairpin, Inverted BsaI Sites
>pSG4K5 (3540 bp)
                                       SEQ ID NO: 30
GAATTCGTTGACAGCTAGCTCAGTCCTAGGTATAATGCTAGCTAGAAGA

GCGACAGGCTCTTCTGTTTTAGAGCTAGAAATAGCAAGTTAAAATAAGG

CTAGTCCGTTATCAACTTGAAAAAGTGGCACCGAGTCGGTGCTTTTTTT

CTAGATAATTGGAGACCGAGCTGGTCTCTCTAGGATGTGCACTAGTAGA

GCTCTGCAGGAGTCACTAAGGGTTAGTTAGTTAGATTAGCAGAAAGTCA

AAAGCCTCCGACCGGAGGCTTTTGACTAAAACTTCCCTTGGGGTTATCA

TTGGGGCTCACTCAAAGGCGGTAATCAGATAAAAAAAATCCTTAGCTTT

CGCTAAGGATGATTTCTGCTAGTATTATTAGAAAAACTCATCGAGCATC

AAATGAAACTGCAATTTATTCATATCAGGATTATCAATACCATATTTTT

GAAAAAGCCGTTTCTGTAATGAAGGAGAAAACTCACCGAGGCAGTTCCA

AAGAATGGCAAGGTCCTGGTAACGGTCTGCGATTCCGACCCGTCCAACA

TCAATACAACCTATTAATTTCCCCTCGTCAAAAATAAGGTTATCAAGTG

AGAAATCACCATGAGTGACGACTGAATCCGGTGAGAATGGCAAGAGCTT

GTGCATTTCTTTCCAGACTTGTTCAACAGGCCAGCCATTACGCTCGTCA

TCAAAATCACTCGCATCAACCAAACCGTTATTCATGCGTGATTGCGCCT

GAGCAAGACGAAATACACGATCGCTGTTAAAAGGACAATTACAAACAGG

AATCGAATGTAACCGGCGCAGGAACACGGCCAGCGCATCAACAATATTT

TCACCTGAATCAGGATATTCTTCTAATACCTGGAAGGCTGTTTTCCCAG

GAATCGCGGTGGTGAGTAACCACGCATCATCAGGAGTACGGATAAAATG

CTTGATGGTCGGGAGAGGCATAAACTCCGTCAGCCAGTTGAGACGGACC

ATCTCATCTGTAACATCATTGGCAACGCTACCTTTGCCATGTTTCAGAA

ACAACTCTGGCGCATCGGGCTTCCCATACAAGCGATAGATTGTCGCACC

TGATTGCCCGACATTATCGCGAGCCCATTTATACCCATATAAATCAGCG

TCCATGTTGGAGTTTAAGCGCGGACGGGAGCAAGACGTTTCCCGTTGAA

TATGGCTCATAACACCCCTTGTATTACTGTTTATGTAAGCAGACAGTTT

TATTGTTCATGATGATATATTTTTATCTTGTGCAATGTAACATCAGAGA

TTTTGAGACACAACGTGGCTTTGTTGAATAAATCGAACTTTTGCTGAGT

TGAAGGATCAGCTCTAGTAGTTACATTGTCGATCTGTTCATGGTGAACA

GCTTTGAATGCACCAAAAACTCGTAAAAGCTCTGATGTATCTATCTTTT

TTACACCGTTTTCATCTGTGCATATGGACAGTTTTCCCTTTGATATGTA

ACGGTGAACAGTTGTTCTACTTTTGTTTGTTAGTCTTGATGCTTCACTG

ATAGATACAAGAGCCATAAGAACCTCAGATCCTTCCGTATTTAGCCAGT

ATGTTCTCTAGTGTGGTTCGTTGTTTTTGCGTGAGCCATGAGAACGAAC

CATTGAGATCATACTTACTTTGCATGTCACTCAAAAATTTTGCCTCAAA

ACTGGTGAGCTGAATTTTTGCAGTTAAAGCATCGTGTAGTGTTTTTCTT

AGTCCGTTATGTAGGTAGGAATCTGATGTAATGGTTGTTGGTATTTTGT

CACCATTCATTTTTATCTGGTTGTTCTCAAGTTCGGTTACGAGATCCAT

TTGTCTATCTAGTTCAACTTGGAAAATCAACGTATCAGTCGGGCGGCCT

CGCTTATCAACCACCAATTTCATATTGCTGTAAGTGTTTAAATCTTTAC

TTATTGGTTTCAAAACCCATTGGTTAAGCCTTTTAAACTCATGGTAGTT

ATTTTCAAGCATTAACATGAACTTAAATTCATCAAGGCTAATCTCTATA

TTTGCCTTGTGAGTTTTCTTTTGTGTTAGTTCTTTTAATAACCACTCAT

AAATCCTCATAGAGTATTTGTTTTCAAAAGACTTAACATGTTCCAGATT

ATATTTTATGAATTTTTTTAACTGGAAAAGATAAGGCAATATCTCTTCA

CTAAAAACTAATTCTAATTTTTCGCTTGAGAACTTGGCATAGTTTGTCC

ACTGGAAAATCTCAAAGCCTTTAACCAAAGGATTCCTGATTTCCACAGT

TCTCGTCATCAGCTCTCTGGTTGCTTTAGCTAATACACCATAAGCATTT

TCCCTACTGATGTTCATCATCTGAGCGTATTGGTTATAAGTGAACGATA

CCGTCCGTTCTTTCCTTGTAGGGTTTTCAATCGTGGGGTTGAGTAGTGC

CACACAGCATAAAATTAGCTTGGTTTCATGCTCCGTTAAGTCATAGCGA

CTAATCGCTAGTTCATTTGCTTTGAAAACAACTAATTCAGACATACATC

TCAATTGGTCTAGGTGATTTTAATCACTATACCAATTGAGATGGGCTAG

TCAATGATAATTACATGTCCTTTTCCTTTGAGTTGTGGGTATCTGTAAA

TTCTGCTAGACCCTTTGCTGGAAAACTTGTAAATTCTGCTAGACCCTCTG

TAAATTCCGCTAGACCTTTGTGTGTTTTTTTGTTTATATTCAAGTGGT

TATAATTTATAGAATAAAGAAAGAATAAAAAAAGATAAAAAGAATAGAT

CCCAGCCCTGTGTATAACTCACTACTTTAGTCAGTTCCGCAGTATTACA

AAAGGATGTCGCAAACGCTGTTTGCTCCTCTACAAAACAGACCTTAAAA

CCCTAAAGGCTTAAGTAGCACCCTCGCAAGCTCGGGCAAATCGCTGAAT

ATTCCTTTTGTCTCCGACCATCAGGCACCTGAGTCGCTGTCTTTTTCGT

GACATTCAGTTCGCTGCGCTCACGGCTCTGGCAGTGAATGGGGGTAAAT

GGCACTACAGGCGCCTTTTATGGATTCATGCAAGGAAACTACCCATAAT

ACAAGAAAGCCCGTCACGGGCTTCTCAGGGCGTTTTATGGCGGGTCTG

CTATGTGGTGCTATCTGACTTTTTGCTGTTCAGCAGTTCCTGCCCTCTG

ATTTTCCAGTCTGACCACTTCGGATTATCCCGTGACAGGTCATTCAGAC

TGGCTAATGCACCCAGTAAGGCAGCGGTATCATCAACAGGCTTACCCGT

CTTACTGTCCCTAGTGCTTGGATTCTCACCAATAAAAAACGCCCGGCGG

CAACCGAGCGTTCTGAACAAATCCAGATGGAGTTCTGAGGTCATTACTG

GATCTATCAACAGGAGTCCAAGCGAGCTCGTAAACTTGGTCTGACAGCT

CTAGCTCCGGCAAAAAACGGGCAAGGTGTCACCACCCTGCCCTTTTC

TTTAAAACCGAAAAGATTACTTCGCGTTTGCCACCTGACGTCTAAGAAA

AGGAATATTCAGCAATTTGCCCGTGCCGAAGAAAGGCCCACCCGTGAAG

GTGAGCCAGTGAGTTGATTGCTACGTAATTAGTTAGTTAGCCCTTAGTG

ACTC
```

What is claimed:

1. A method of editing a target sequence in a genome of a prokaryotic cell, the method comprising:
   introducing a first nucleotide sequence encoding into the prokaryotic cell, a nicking nuclease, wherein the nicking nuclease is a Cas9 mutant;
   introducing at least one second nucleotide sequence encoding two crRNAs into the prokaryotic cell, wherein each crRNA comprises at least one guide sequence complementary to a region of the target sequence of the prokaryotic genome, wherein the region of the target sequence of the prokaryotic genome is less than 100 nucleotides from a repeated sequence of the prokaryotic genome and is adjacent to a protospacer adjacent motif (PAM);
   coexpressing the first nucleotide sequence and the at least one second nucleotide sequence in the prokaryotic cell to generate a transformed prokaryotic cell; and
   culturing the transformed prokaryotic cell to remove the target sequence from the genome of the cultured prokaryotic cell, wherein the method generates only single-stranded breaks in genome of the prokaryotic cell.

2. The method of claim 1, wherein at least one pair of crRNAs that comprise guide sequences complementary to the 5' end and 3' end of the target sequence is introduced into the prokaryotic cell, culturing the transformed prokaryote deletes the target sequence from the genome of the prokaryotic cell.

3. The method of claim 1, further comprising introducing a third nucleotide sequence encoding a donor sequence, wherein the donor sequence comprises the repeated sequence of the prokaryotic genome, and a replacement sequence.

4. The method of claim 3, wherein the coexpressing step further comprises coexpressing the third nucleotide sequence in the prokaryotic cell, culturing the transformed prokaryotic cell replaces the target sequence with the replacement sequence in the genome of the cultured prokaryotic cell.

5. The method of claim 1, wherein the target sequence is less than 50 nucleotides from the repeated sequence or homologous sequence of the prokaryotic genome.

6. The method of claim 1, wherein the target sequence is between 20 nucleotides to 40 nucleotides from the repeated sequence or homologous sequence of the prokaryotic genome.

7. The method of claim 1, wherein the target sequence is 20 nucleotides from the repeated sequence or homologous sequence of the prokaryotic genome.

8. The method of claim 1, wherein the crRNA is an sgRNA comprising an 18-22 nucleotide-long guide sequence.

9. The method of claim 1, wherein the Cas9 mutant comprises either a mutation in its RuvCl nuclease domain or a mutation in its HNH nuclease domain.

10. The method of claim 9, wherein the mutation is a D10A substitution.

11. The method of claim 9, wherein the mutation is a H840A substitution.

12. The method of claim 1, wherein 36 Kb to 97 Kb of the genome of the prokaryotic cell is deleted or replaced.

13. The method of claim 1, wherein 36 Kb of the genome of the prokaryotic cell is deleted or replaced.

14. The method of claim 1, wherein 97 Kb of the genome of the prokaryotic cell is deleted or replaced.

15. The method of claim 1, wherein two crRNAs are introduced into the prokaryotic cell and each crRNA comprises one guide sequence.

16. The method of claim 1, wherein the prokaryotic cell is *Escherichia coli*.

* * * * *

SEQUENCE LISTING

<160> NUMBER OF SEQ ID NOS: 49

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
tgccacctga cgtctaagaa                                                    20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
aataccgcct ttgagtgagc                                                    20

<210> SEQ ID NO 3
<211> LENGTH: 31
<212> TYPE: DNA
<213> ORGANISM: Artificial Sequence
<220> FEATURE:
<223> OTHER INFORMATION: primer

<400> SEQUENCE: 3
atgctcttca gctatcggca caaatagcgt c                                       31

<210> SEQ ID NO 4
<211> LENGTH: 38
<212> TYPE: DNA
<213> ORGANISM: Artificial Sequence
<220> FEATURE:
<223> OTHER INFORMATION: primer

<400> SEQUENCE: 4
gagctcttcg agctaagcct attgagtatt tcttatcc                                38

<210> SEQ ID NO 5
<211> LENGTH: 34
<212> TYPE: DNA
<213> ORGANISM: Artificial Sequence
<220> FEATURE:
<223> OTHER INFORMATION: primer

<400> SEQUENCE: 5
gagctcttcg gccattgttc cacaaagttt cctt                                    34

<210> SEQ ID NO 6
<211> LENGTH: 37
<212> TYPE: DNA
<213> ORGANISM: Artificial Sequence
<220> FEATURE:
<223> OTHER INFORMATION: primer

<400> SEQUENCE: 6
atgctcttca ggcatcgaca tcataatcac ttaaacg                                 37

<210> SEQ ID NO 7
<211> LENGTH: 34
<212> TYPE: DNA
<213> ORGANISM: Artificial Sequence

```
<220> FEATURE:
<223> OTHER INFORMATION: primer

<400> SEQUENCE: 7
cgccatattc atggtaggaa tcaatgcctg agtg                                 34

<210> SEQ ID NO 8
<211> LENGTH: 34
<212> TYPE: DNA
<213> ORGANISM: Artificial Sequence
<220> FEATURE:
<223> OTHER INFORMATION: primer

<400> SEQUENCE: 8
ggcatcaaca gcacattcag tggtttaccg tgcg                                 34

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
gctacgtgtt atgaacttcg aaga                                            24

<210> SEQ ID NO 10
<211> LENGTH: 35
<212> TYPE: DNA
<213> ORGANISM: Artificial Sequence
<220> FEATURE:
<223> OTHER INFORMATION: primer

<400> SEQUENCE: 10
acatttacgc gattaatact gcgcgtaata taatt                                35

<210> SEQ ID NO 11
<211> LENGTH: 35
<212> TYPE: DNA
<213> ORGANISM: Artificial Sequence
<220> FEATURE:
<223> OTHER INFORMATION: primer

<400> SEQUENCE: 11
acatctggtg gcgctaataa atctggcaag tcaca                                35

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
ccagccaggc taagcctcaa gcacaggtca atatc                                35

<210> SEQ ID NO 13
<211> LENGTH: 35
<212> TYPE: DNA
<213> ORGANISM: Artificial Sequence
<220> FEATURE:
<223> OTHER INFORMATION: primer

<400> SEQUENCE: 13
cggctttggt cataataata atattgcggt ggcgt                                35
```

<210> SEQ ID NO 14
<211> LENGTH: 27
<212> TYPE: DNA
<213> ORGANISM: Artificial Sequence
<220> FEATURE:
<223> OTHER INFORMATION: primer

<400> SEQUENCE: 14
ggatttcctt aactgcttct cctcacc                                27

<210> SEQ ID NO 15
<211> LENGTH: 27
<212> TYPE: DNA
<213> ORGANISM: Artificial Sequence
<220> FEATURE:
<223> OTHER INFORMATION: primer

<400> SEQUENCE: 15
attaccaata aagaatcgtc tggcggt                                27

<210> SEQ ID NO 16
<211> LENGTH: 27
<212> TYPE: DNA
<213> ORGANISM: Artificial Sequence
<220> FEATURE:
<223> OTHER INFORMATION: primer

<400> SEQUENCE: 16
ttatcaggct cctccagata attgtcg                                27

<210> SEQ ID NO 17
<211> LENGTH: 29
<212> TYPE: DNA
<213> ORGANISM: Artificial Sequence
<220> FEATURE:
<223> OTHER INFORMATION: primer

<400> SEQUENCE: 17
gtctgcacaa ggattacatc atgattatg                              29

<210> SEQ ID NO 18
<211> LENGTH: 29
<212> TYPE: DNA
<213> ORGANISM: Artificial Sequence
<220> FEATURE:
<223> OTHER INFORMATION: primer

<400> SEQUENCE: 18
gcaggggtac ccggtcgatg ggttgtgtc                              29

<210> SEQ ID NO 19
<211> LENGTH: 34
<212> TYPE: DNA
<213> ORGANISM: Artificial Sequence
<220> FEATURE:
<223> OTHER INFORMATION: primer

<400> SEQUENCE: 19
cgtcatgtca ctagtcgagg cgggtaatta gaca                        34

<210> SEQ ID NO 20
<211> LENGTH: 35
<212> TYPE: DNA
<213> ORGANISM: Artificial Sequence
<220> FEATURE:
<223> OTHER INFORMATION: primer

```
<400> SEQUENCE: 20
gcaggattca ctagtcctac taccagaacg acggc                              35

<210> SEQ ID NO 21
<211> LENGTH: 35
<212> TYPE: DNA
<213> ORGANISM: Artificial Sequence
<220> FEATURE:
<223> OTHER INFORMATION: primer

<400> SEQUENCE: 21
cgtgttcgcc tcgagactgc ggtacgtctg gcaat                              35

<210> SEQ ID NO 22
<211> LENGTH: 32
<212> TYPE: DNA
<213> ORGANISM: Artificial Sequence
<220> FEATURE:
<223> OTHER INFORMATION: primer

<400> SEQUENCE: 22
gcaagtttcc tcgagggcgg aaggggaga aa                                  32

<210> SEQ ID NO 23
<211> LENGTH: 34
<212> TYPE: DNA
<213> ORGANISM: Artificial Sequence
<220> FEATURE:
<223> OTHER INFORMATION: primer

<400> SEQUENCE: 23
cgtggtattg gcgcctctgg ggagagggtt aggg                               34

<210> SEQ ID NO 24
<211> LENGTH: 38
<212> TYPE: DNA
<213> ORGANISM: Artificial Sequence
<220> FEATURE:
<223> OTHER INFORMATION: primer

<400> SEQUENCE: 24
cgtggtattg gatcctttgt gggccattaa caccacct                           38

<210> SEQ ID NO 25
<211> LENGTH: 37
<212> TYPE: DNA
<213> ORGANISM: Artificial Sequence
<220> FEATURE:
<223> OTHER INFORMATION: primer

<400> SEQUENCE: 25
cctatgatca ctagttgggt cgatcttgtc gacaaag                            37

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
ctcattcgaa accacccacc g                                             21

<210> SEQ ID NO 27
```

```
<211> LENGTH: 22
<212> TYPE: DNA
<213> ORGANISM: Artificial Sequence
<220> FEATURE:
<223> OTHER INFORMATION: primer

<400> SEQUENCE: 27
gatcatcatg tttattgcgt gg                                              22

<210> SEQ ID NO 28
<211> LENGTH: 32
<212> TYPE: DNA
<213> ORGANISM: Artificial Sequence
<220> FEATURE:
<223> OTHER INFORMATION: primer

<400> SEQUENCE: 28
catggtctca aattaagcag ctctaatgcg ct                                   32

<210> SEQ ID NO 29
<211> LENGTH: 36
<212> TYPE: DNA
<213> ORGANISM: Artificial Sequence
<220> FEATURE:
<223> OTHER INFORMATION: primer

<400> SEQUENCE: 29
gacatgtcta gacaacttaa atgtgaaagt gggtct                               36

<210> SEQ ID NO 30
<211> LENGTH: 3581
<212> TYPE: DNA
<213> ORGANISM: Artificial Sequence
<220> FEATURE:
<223> OTHER INFORMATION: plasmid vector

<400> SEQUENCE: 30
gaattcgttg acagctagct cagtcctagg tataatgcta gctagaagag cgacaggctc       60
ttctgtttta gagctagaaa tagcaagtta aaataaggct agtccgttat caacttgaaa      120
aagtggcacc gagtcggtgc ttttttttcta gataattgga gaccgagctg gtctctctag     180
gatgtgcact agtagagctc tgcaggagtc actaagggtt agttagttag attagcagaa      240
agtcaaaagc ctccgaccgg aggcttttga ctaaaacttc ccttgggtt atcattgggg       300 ctcactcaaa ggcggtaatc agataaaaaa aatccttagc tttcgctaag gatgatttct      360
gctagtatta ttagaaaaac tcatcgagca tcaaatgaaa ctgcaattta ttcatatcag      420
gattatcaat accatatttt tgaaaaagcc gtttctgtaa tgaaggagaa aactcaccga      480
ggcagttcca agaatggca aggtcctggt aacggtctgc gattccgacc cgtccaacat       540
caatacaacc tattaatttc ccctcgtcaa aaataaggtt atcaagtgag aaatcaccat      600
gagtgacgac tgaatccggt gagaatggca agagcttgtg catttctttc cagacttgtt      660
caacaggcca gccattacgc tcgtcatcaa aatcactcgc atcaaccaaa ccgttattca      720
tgcgtgattg cgcctgagca agacgaaata cacgatcgct gttaaaagga caattacaaa      780
caggaatcga atgtaaccgg cgcaggaaca cggccagcgc atcaacaata ttttcacctg      840
aatcaggata ttcttctaat acctggaagg ctgttttccc aggaatcgcg gtggtgagta      900
accacgcatc atcaggagta cggataaaat gcttgatggt cgggagaggc ataaactccg      960
tcagccagtt gagacggacc atctcatctg taacatcatt ggcaacgcta cctttgccat     1020
gtttcagaaa caactctggc gcatcgggct tcccatacaa gcgatagatt gtcgcacctg     1080
```

```
attgcccgac attatcgcga gcccatttat acccatataa atcagcgtcc atgttggagt    1140
ttaagcgcgg acgggagcaa gacgtttccc gttgaatatg gctcataaca cccttgtat     1200 tactgtttat gtaagcagac agttttattg ttcatgatga tatattttta tcttgtgcaa    1260
tgtaacatca gagattttga gacacaacgt ggctttgttg aataaatcga acttttgctg    1320
agttgaagga tcagctctag tagttacatt gtcgatctgt tcatggtgaa cagctttgaa    1380
tgcaccaaaa actcgtaaaa gctctgatgt atctatcttt tttacaccgt tttcatctgt    1440
gcatatggac agttttccct ttgatatgta acggtgaaca gttgttctac ttttgtttgt    1500
tagtcttgat gcttcactga tagatacaag agccataaga acctcagatc cttccgtatt    1560
tagccagtat gttctctagt gtggttcgtt gtttttgcgt gagccatgag aacgaaccat    1620
tgagatcata cttactttgc atgtcactca aaaattttgc ctcaaaactg gtgagctgaa    1680
tttttgcagt taaagcatcg tgtagtgttt ttcttagtcc gttatgtagg taggaatctg    1740
atgtaatggt tgttggtatt ttgtcaccat tcatttttat ctggttgttc tcaagttcgg    1800
ttacgagatc catttgtcta tctagttcaa cttggaaaat caacgtatca gtcgggcggc    1860
ctcgcttatc aaccaccaat ttcatattgc tgtaagtgtt taaatcttta cttattggtt    1920
tcaaacccca ttggttaagc cttttaaact catggtagtt attttcaagc attaacatga    1980
acttaaattc atcaaggcta atctctatat ttgccttgtg agttttcttt tgtgttagtt    2040
cttttaataa ccactcataa atcctcatag agtatttgtt ttcaaaagac ttaacatgtt    2100
ccagattata ttttatgaat ttttttaact ggaaaagata aggcaatatc tcttcactaa    2160
aaactaattc taattttttcg cttgagaact tggcatagtt tgtccactgg aaaatctcaa    2220
agcctttaac caaaggattc ctgatttcca cagttctcgt catcagctct ctggttgctt    2280
tagctaatac accataagca ttttccctac tgatgttcat catctgagcg tattggttat    2340
aagtgaacga taccgtccgt tcttttccttg tagggttttc aatcgtgggg ttgagtagtg    2400
ccacacagca taaattagc ttggtttcat gctccgttaa gtcatagcga ctaatcgcta     2460
gttcatttgc tttgaaaaca actaattcag acatacatct caattggtct aggtgatttt    2520
aatcactata ccaattgaga tgggctagtc aatgataatt acatgtcctt ttccttttgag   2580 ttgtgggtat ctgtaaattc tgctagacct ttgctggaaa acttgtaaat tctgctagac    2640
cctctgtaaa ttccgctaga ccttttgtgtg ttttttttgt ttatattcaa gtggttataa   2700
tttatagaat aaagaaagaa taaaaaaaga taaaagaat agatcccagc cctgtgtata    2760
actcactact ttagtcagtt ccgcagtatt acaaaaggat gtcgcaaacg ctgtttgctc    2820
ctctacaaaa cagaccttaa aaccctaaag gcttaagtag caccctcgca agctcgggca    2880
aatcgctgaa tattccttttt gtctccgacc atcaggcacc tgagtcgctg tcttttttcgt   2940 gacattcagt tcgctgcgct cacggctctg gcagtgaatg ggggtaaatg gcactacagg    3000 cgcctttat ggattcatgc aaggaaacta cccataatac aagaaaagcc cgtcacgggc     3060
ttctcagggc gttttatggc gggtctgcta tgtggtgcta tctgactttt tgctgttcag    3120
cagttcctgc cctctgattt tccagtctga ccacttcgga ttatcccgtg acaggtcatt    3180
cagactggct aatgcaccca gtaaggcagc ggtatcatca acaggcttac ccgtcttact    3240
gtccctagtg cttggattct caccaataaa aaacgcccgg cggcaaccga gcgttctgaa    3300
caaatccaga tggagttctg aggtcattac tggatctatc aacaggagtc caagcgagct    3360
cgtaaacttg gtctgacagc tctagctccg gcaaaaaaac gggcaaggtg tcaccaccct    3420
```

```
gcccttttc  tttaaaaccg  aaaagattac  ttcgcgtttg  ccacctgacg  tctaagaaaa    3480
ggaatattca  gcaatttgcc  cgtgccgaag  aaaggcccac  ccgtgaaggt  gagccagtga    3540
gttgattgct  acgtaattag  ttagttagcc  cttagtgact  c                         3581
```

<210> SEQ ID NO 31
<211> LENGTH: 21
<212> TYPE: DNA
<213> ORGANISM: Artificial Sequence
<220> FEATURE:
<223> OTHER INFORMATION: short guide sequence

<400> SEQUENCE: 31
agaagagcga caggctcttc t        21

<210> SEQ ID NO 32
<211> LENGTH: 21
<212> TYPE: DNA
<213> ORGANISM: Artificial Sequence
<220> FEATURE:
<223> OTHER INFORMATION: short guide sequence

<400> SEQUENCE: 32
accatctaat tcaacaagaa t        21

<210> SEQ ID NO 33
<211> LENGTH: 20
<212> TYPE: DNA
<213> ORGANISM: Artificial Sequence
<220> FEATURE:
<223> OTHER INFORMATION: short guide sequence

<400> SEQUENCE: 33
aaaggagaag aacttttcac          20

<210> SEQ ID NO 34
<211> LENGTH: 21
<212> TYPE: DNA
<213> ORGANISM: Artificial Sequence
<220> FEATURE:
<223> OTHER INFORMATION: short guide sequence

<400> SEQUENCE: 34
accaattctt gttgaattag a        21

<210> SEQ ID NO 35
<211> LENGTH: 21
<212> TYPE: DNA
<213> ORGANISM: Artificial Sequence
<220> FEATURE:
<223> OTHER INFORMATION: short guide sequence

<400> SEQUENCE: 35
attcaagagt gccatgcccg a        21

<210> SEQ ID NO 36
<211> LENGTH: 21
<212> TYPE: DNA
<213> ORGANISM: Artificial Sequence
<220> FEATURE:
<223> OTHER INFORMATION: short guide sequence

<400> SEQUENCE: 36
aggtattgat tttaaagaag a        21

<210> SEQ ID NO 37
<211> LENGTH: 21
<212> TYPE: DNA
<213> ORGANISM: Artificial Sequence
<220> FEATURE:
<223> OTHER INFORMATION: short guide sequence

<400> SEQUENCE: 37
acaacgaaaa gagagaccac a                                              21

<210> SEQ ID NO 38
<211> LENGTH: 20
<212> TYPE: DNA
<213> ORGANISM: Artificial Sequence
<220> FEATURE:
<223> OTHER INFORMATION: short guide sequence

<400> SEQUENCE: 38
aaattgtggt gttctaggga                                                20

<210> SEQ ID NO 39
<211> LENGTH: 20
<212> TYPE: DNA
<213> ORGANISM: Artificial Sequence
<220> FEATURE:
<223> OTHER INFORMATION: short guide sequence

<400> SEQUENCE: 39
acaccacaat ttcgctctct                                                20

<210> SEQ ID NO 40
<211> LENGTH: 21
<212> TYPE: DNA
<213> ORGANISM: Artificial Sequence
<220> FEATURE:
<223> OTHER INFORMATION: short guide sequence

<400> SEQUENCE: 40
accgggtaac cacgacccag t                                              21

<210> SEQ ID NO 41
<211> LENGTH: 21
<212> TYPE: DNA
<213> ORGANISM: Artificial Sequence
<220> FEATURE:
<223> OTHER INFORMATION: short guide sequence

<400> SEQUENCE: 41
atgagaagtt aaataaccat g                                              21

<210> SEQ ID NO 42
<211> LENGTH: 21
<212> TYPE: DNA
<213> ORGANISM: Artificial Sequence
<220> FEATURE:
<223> OTHER INFORMATION: short guide sequence

<400> SEQUENCE: 42
actccgagaa tcataaatac a                                              21

<210> SEQ ID NO 43
<211> LENGTH: 20
<212> TYPE: DNA
<213> ORGANISM: Artificial Sequence
<220> FEATURE:
<223> OTHER INFORMATION: short guide sequence

```
<400> SEQUENCE: 43
aactacgccg atctgttgct                                               20

<210> SEQ ID NO 44
<211> LENGTH: 20
<212> TYPE: DNA
<213> ORGANISM: Artificial Sequence
<220> FEATURE:
<223> OTHER INFORMATION: short guide sequence

<400> SEQUENCE: 44
aatttttgtt ttattaagga                                               20

<210> SEQ ID NO 45
<211> LENGTH: 20
<212> TYPE: DNA
<213> ORGANISM: Artificial Sequence
<220> FEATURE:
<223> OTHER INFORMATION: short guide sequence

<400> SEQUENCE: 45
attctgatac ggttgttgat                                               20

<210> SEQ ID NO 46
<211> LENGTH: 21
<212> TYPE: DNA
<213> ORGANISM: Artificial Sequence
<220> FEATURE:
<223> OTHER INFORMATION: short guide sequence

<400> SEQUENCE: 46
atggcgacta tgcactaggg a                                             21

<210> SEQ ID NO 47
<211> LENGTH: 21
<212> TYPE: DNA
<213> ORGANISM: Artificial Sequence
<220> FEATURE:
<223> OTHER INFORMATION: short guide sequence

<400> SEQUENCE: 47
agtgcatagt cgccaccatt c                                             21

<210> SEQ ID NO 48
<211> LENGTH: 21
<212> TYPE: DNA
<213> ORGANISM: Artificial Sequence
<220> FEATURE:
<223> OTHER INFORMATION: short guide sequence

<400> SEQUENCE: 48
attagcactt tcctctacca a                                             21

<210> SEQ ID NO 49
<211> LENGTH: 20
<212> TYPE: DNA
<213> ORGANISM: Artificial Sequence
<220> FEATURE:
<223> OTHER INFORMATION: short guide sequence

<400> SEQUENCE: 49
attattgtgc atttcactac                                               20
```